United States Patent
Wasicek et al.

(10) Patent No.: US 10,335,319 B2
(45) Date of Patent: Jul. 2, 2019

(54) METHOD AND APPARATUS FOR CLEANING ISTHMUS OF EUSTACHIAN TUBE

(71) Applicant: Acclarent, Inc., Menlo Park, CA (US)

(72) Inventors: Lawrence D. Wasicek, San Jose, CA (US); Sivette Lam, Milpitas, CA (US); Ketan P. Muni, San Jose, CA (US)

(73) Assignee: Acclarent, Inc., Irvine, CA (US)

( * ) Notice: Subject to any disclaimer, the term of this patent is extended or adjusted under 35 U.S.C. 154(b) by 249 days.

(21) Appl. No.: 14/919,991

(22) Filed: Oct. 22, 2015

(65) Prior Publication Data

US 2016/0287445 A1    Oct. 6, 2016

Related U.S. Application Data

(60) Provisional application No. 62/139,919, filed on Mar. 30, 2015.

(51) Int. Cl.
*A61F 11/00*   (2006.01)
*A61M 25/10*   (2013.01)
(Continued)

(52) U.S. Cl.
CPC .......... *A61F 11/006* (2013.01); *A61B 1/0661* (2013.01); *A61B 1/227* (2013.01);
(Continued)

(58) Field of Classification Search
CPC ....... A61B 90/70; A61B 1/0661; A61B 1/227; A61B 17/24; A61M 39/19;
(Continued)

(56) References Cited

U.S. PATENT DOCUMENTS

| 5,320,617 A * | 6/1994 | Leach ............... A61B 18/24 |
| | | 128/898 |
| 6,716,813 B2 | 4/2004 | Lim et al. |
| | | (Continued) |

FOREIGN PATENT DOCUMENTS

CN    203 029 796 U    7/2013

OTHER PUBLICATIONS

St. Croix, B., et al., "Genes Expressed in Human Tumor Endothelium," Science, Aug. 18, 2000, vol. 289, pp. 1197-1201, 6 pgs.

(Continued)

*Primary Examiner* — Richard G Louis
(74) *Attorney, Agent, or Firm* — Frost Brown Todd LLC

(57) ABSTRACT

A method for cleaning an isthmus of a Eustachian tube (ET) of a patient includes using an instrument. The instrument includes a proximal portion, a distal portion, and a shaft extending therebetween, and a treatment feature disposed at the distal portion. The method includes directing the instrument into an oro-nasal cavity of the patient and advancing at least the distal portion of the instrument into an opening of the ET. The method further includes further advancing the instrument within the ET so that the treatment feature is disposed past, or is coincident with, the isthmus. The method further includes moving the treatment feature relative to the isthmus to clean the isthmus.

20 Claims, 20 Drawing Sheets

(51) Int. Cl.
  *A61B 1/06*     (2006.01)
  *A61B 1/227*    (2006.01)
  *A61M 25/00*    (2006.01)
  *A61M 25/01*    (2006.01)
  *A61M 29/02*    (2006.01)
  *A61B 17/24*    (2006.01)
  *A61B 18/14*    (2006.01)
  *A61B 17/22*    (2006.01)
  *A61B 17/00*    (2006.01)
  *A61B 17/32*    (2006.01)
  *A61B 18/00*    (2006.01)
  *A61N 7/00*     (2006.01)

(52) U.S. Cl.
  CPC .......... *A61B 17/24* (2013.01); *A61B 18/1492* (2013.01); *A61F 11/002* (2013.01); *A61M 25/0043* (2013.01); *A61M 25/01* (2013.01); *A61M 25/10184* (2013.11); *A61M 29/02* (2013.01); *A61B 17/22* (2013.01); *A61B 2017/00358* (2013.01); *A61B 2017/00787* (2013.01); *A61B 2017/22014* (2013.01); *A61B 2017/22021* (2013.01); *A61B 2017/22034* (2013.01); *A61B 2017/320012* (2013.01); *A61B 2018/00285* (2013.01); *A61B 2018/00327* (2013.01); *A61N 2007/0043* (2013.01)

(58) Field of Classification Search
  CPC ........ A61M 25/10184; A61M 25/0043; A61M 25/01; A61M 29/02; A61F 11/006; A61F 11/002
  USPC ....................................................... 606/161
  See application file for complete search history.

(56) References Cited

U.S. PATENT DOCUMENTS

| | | | |
|---|---|---|---|
| 7,803,150 B2 | 9/2010 | Chang et al. | |
| 9,155,492 B2 | 10/2015 | Jenkins et al. | |
| 2005/0240147 A1* | 10/2005 | Makower | A61B 17/24 604/96.01 |
| 2006/0063973 A1 | 3/2006 | Makower et al. | |
| 2006/0095066 A1* | 5/2006 | Chang | A61B 17/1204 606/199 |
| 2008/0154343 A1* | 6/2008 | Li | A61B 18/22 607/89 |
| 2008/0275483 A1* | 11/2008 | Makower | A61B 17/24 606/192 |
| 2009/0163890 A1* | 6/2009 | Clifford | A61B 1/227 604/514 |
| 2010/0030031 A1 | 2/2010 | Goldfarb et al. | |
| 2010/0198191 A1 | 8/2010 | Clifford et al. | |
| 2010/0274188 A1* | 10/2010 | Chang | A61B 1/227 604/96.01 |
| 2011/0288477 A1* | 11/2011 | Ressemann | G06F 17/30516 604/95.04 |
| 2013/0274715 A1 | 10/2013 | Chan et al. | |
| 2015/0374963 A1 | 12/2015 | Chan et al. | |

OTHER PUBLICATIONS

International Search Report and Written Opinion dated Jul. 18, 2016 for Application No. PCT/US2016/024720, 13 pgs.
U.S. Appl. No. 62/139,919, filed Mar. 30, 2015.

\* cited by examiner

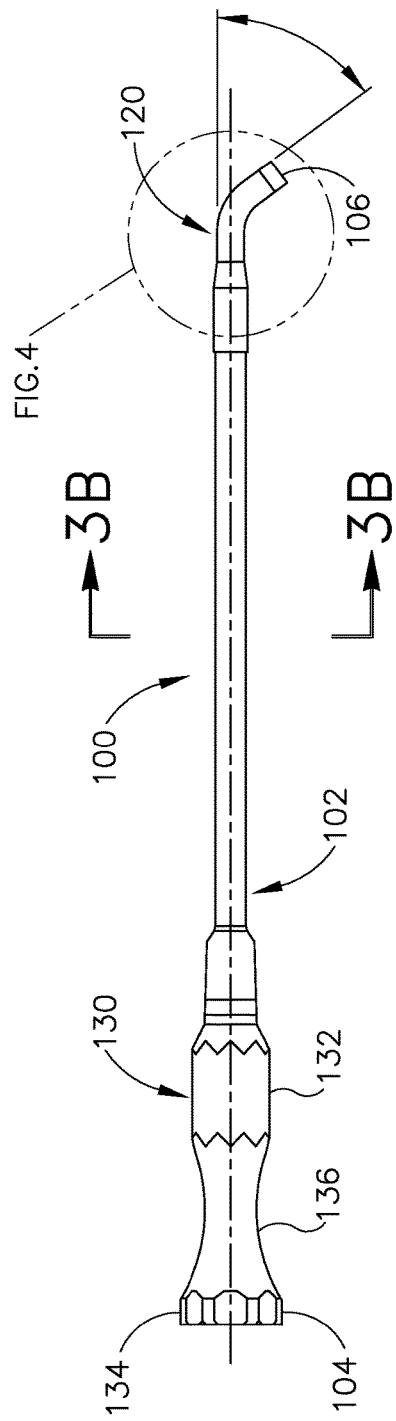
Fig.3A
Fig.3B
Fig.4

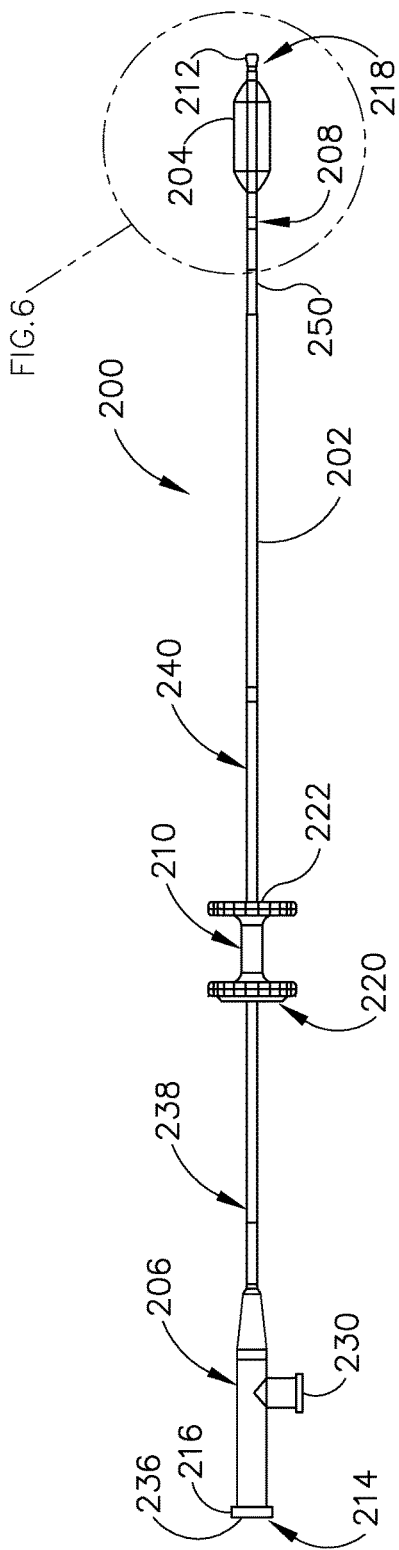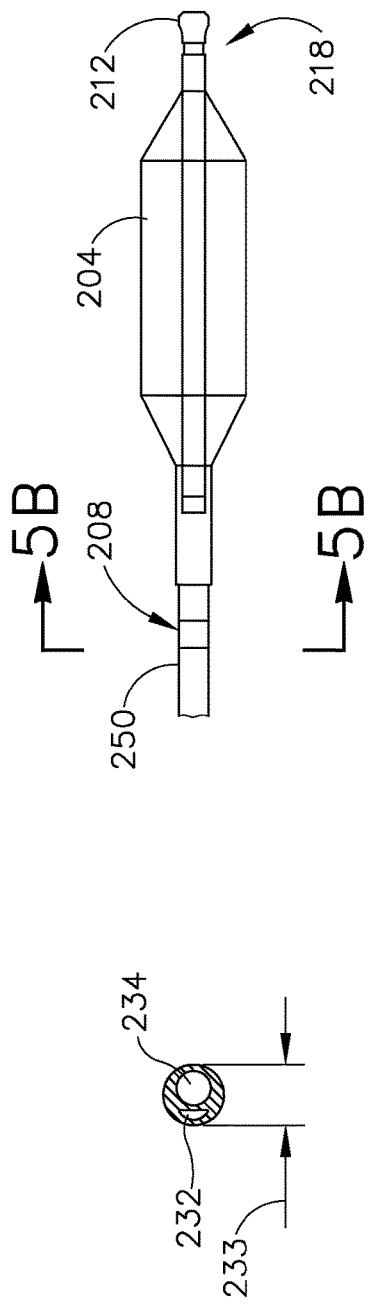
Fig.5A
Fig.5B
Fig.6

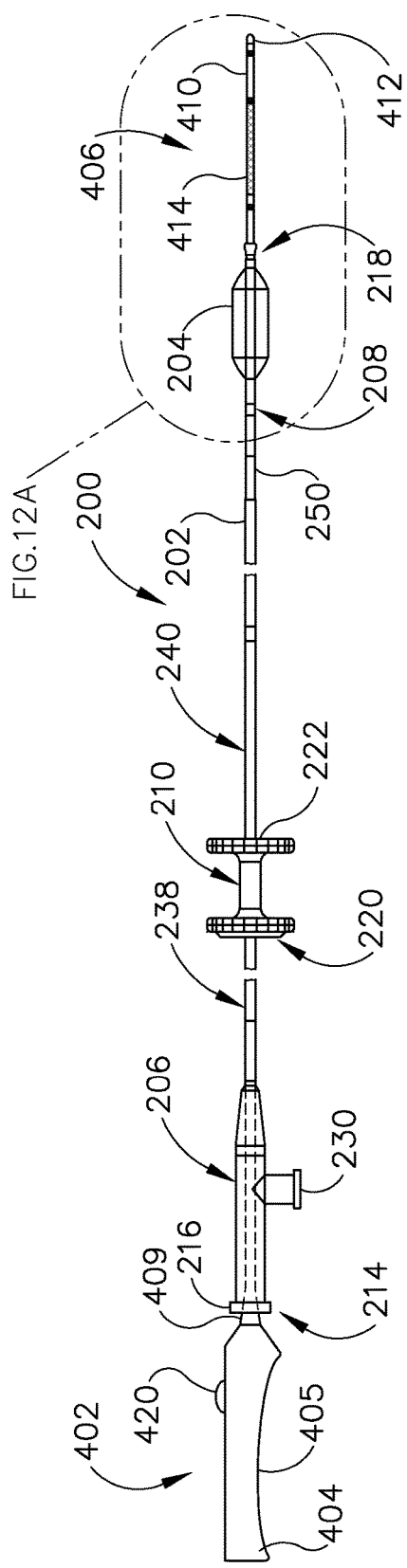
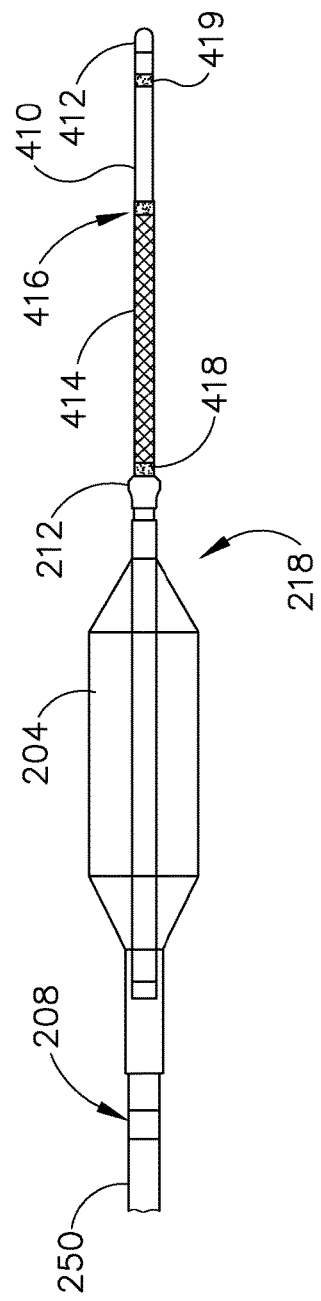
Fig.12
Fig.12A

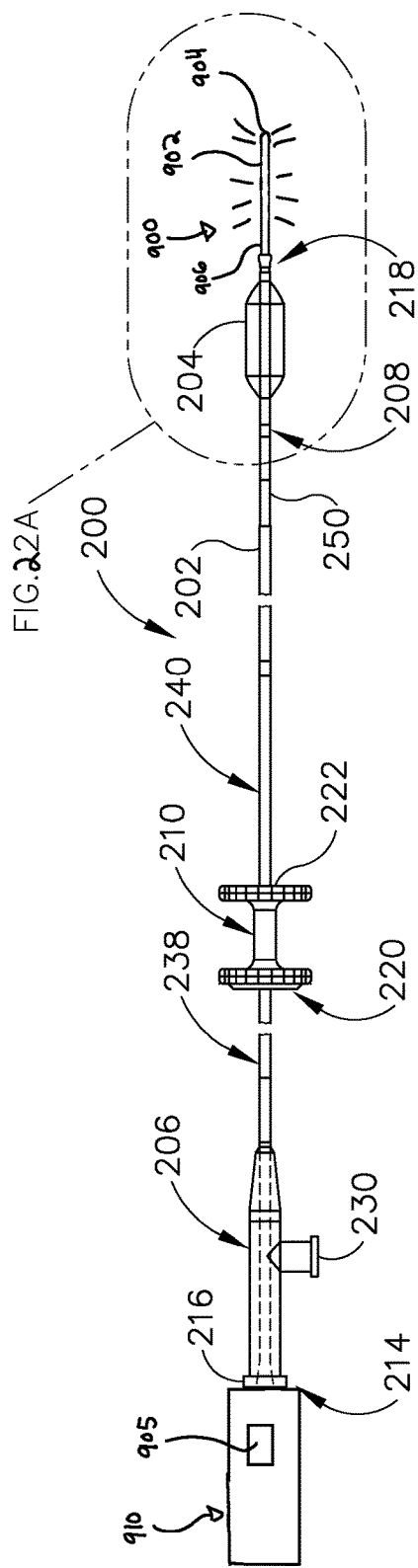
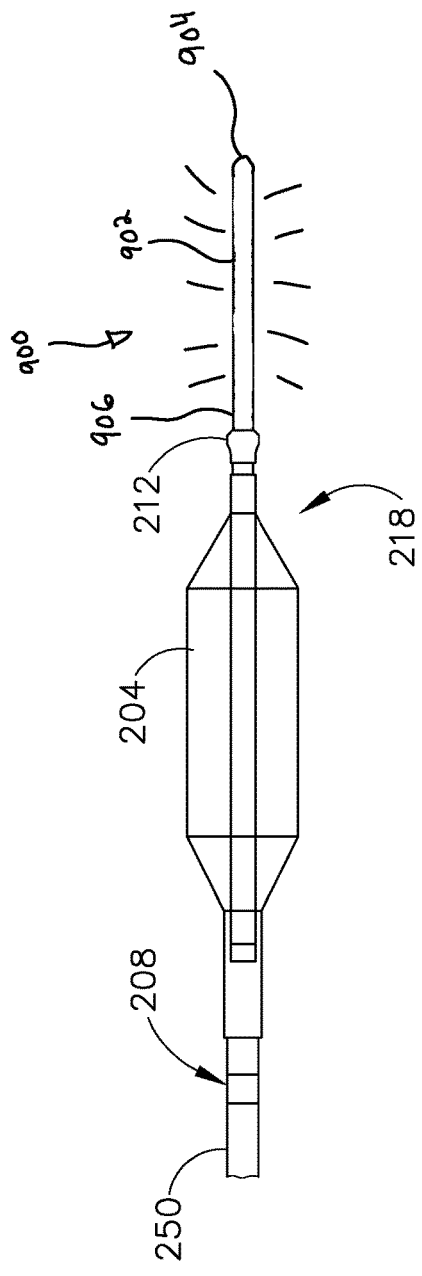
Fig. 22
Fig. 22A

METHOD AND APPARATUS FOR CLEANING ISTHMUS OF EUSTACHIAN TUBE

PRIORITY

This application claims priority to U.S. Provisional Patent Application No. 62/139,919, entitled "Method and Apparatus for Cleaning Isthmus of Eustachian Tube," filed Mar. 30, 2015, the disclosure of which is incorporated by reference herein.

BACKGROUND

Referring to FIGS. 1-2, the ear (10) is divided into three parts: an external ear (12), a middle ear (14) and an inner ear (16). The external ear (12) consists of an auricle (18) and ear canal (20) that gather sound and direct it toward a tympanic membrane (22) (also referred to as the eardrum) located at an inner end (24) of the ear canal (20). The middle ear (14) lies between the external and inner ears (12, 16) and is connected to the back of the throat by a Eustachian tube (ET) (26), which serves as a pressure equalizing valve between the ear (10) and the sinuses. The ET (26) terminates in a pharyngeal ostium (28) in the nasopharynx region (30) of the throat (32). In addition to the eardrum (22), the middle ear (14) also consists of three small ear bones (ossicles): the malleus (34) (hammer), incus (36) (anvil) and stapes (38) (stirrup). These bones (34, 36, 38) transmit sound vibrations to the inner ear (16) and thereby act as a transformer, converting sound vibrations in the canal (20) of the external ear (12) into fluid waves in the inner ear (16). These fluid waves stimulate several nerve endings (40) that, in turn, transmit sound energy to the brain where it is interpreted.

The ET (26) is a narrow, one-and-a-half inch long channel connecting the middle ear (14) with the nasopharynx (30), the upper throat area just above the palate, in back of the nose. The ET (26) functions as a pressure equalizing valve for the middle ear (14), which is normally filled with air. When functioning properly, the ET (26) opens for a fraction of a second periodically (about once every three minutes) in response to swallowing or yawning. In so doing, it allows air into the middle ear (14) to replace air that has been absorbed by the middle ear lining (mucous membrane) or to equalize pressure changes occurring on altitude changes. Anything that interferes with this periodic opening and closing of the ET (26) may result in hearing impairment or other ear symptoms.

Obstruction or blockage of the ET (26) results in a negative middle ear (14) pressure, with retraction (sucking in) of the eardrum (22). In adults, this is usually accompanied by some ear discomfort, a fullness or pressure feeling and may result in a mild hearing impairment and head noise (tinnitus). There may be no symptoms in children. If the obstruction is prolonged, fluid may be drawn from the mucous membrane of the middle ear (14), creating a condition referred to as serous otitis media (fluid in the middle ear). This occurs frequently in children in connection with an upper respiratory infection and accounts for the hearing impairment associated with this condition.

A lining membrane (mucous membrane) of the middle ear (14) and ET (26) is connected with, and is the same as, the membrane of the nose (42), sinuses (44) and throat (32). Infection of these areas results in mucous membrane swelling which in turn may result in obstruction of the ET (26). This is referred to as serous otitis media, which as discussed above is essentially a collection of fluid in the middle ear (14). Serous otitis media can be acute or chronic, and may be the result of blockage of the pharyngeal ostium (28) of the ET (26), which leads to the accumulation of fluid in the middle ear (14). In the presence of bacteria, this fluid may become infected, leading to an acute suppurative otitis media (infected or abscessed middle ear). When infection does not develop, the fluid remains until the ET (26) again begins to function normally, at which time the fluid is absorbed or drains down the tube into the throat (32) through the ET (26) pharyngeal ostium (28).

Chronic serous otitis media may result from longstanding ET blockage, or from thickening of the fluid so that it cannot be absorbed or drained down the ET (26). This chronic condition may lead to hearing impairment. There may be recurrent ear pain, especially when the individual catches a cold. Fortunately, serous otitis media may persist for many years without producing any permanent damage to the middle ear mechanism. The presence of fluid in the middle ear (14), however, makes it very susceptible to recurrent acute infections. These recurrent infections may result in middle ear damage.

When the ET (26) contains a build-up of fluid, a number of things may occur. First, the body may absorb the air from the middle ear (14), causing a vacuum to form that tends to pull the lining membrane and ear drum (22) inwardly, causing pain. Next, the body may replace the vacuum with more fluid which tends to relieve the pain, but the patient can experience a fullness sensation in the ear (10). Treatment of this condition with antihistamines and decongestants can take many weeks to be fully effective. Finally, the fluid can become infected, which can lead to pain, illness, and temporary hearing loss. If the inner ear (14) is affected, the patient may feel a spinning or turning sensation (vertigo). The infection may be treated with antibiotics.

However, even if antihistamines, decongestants, and antibiotics are used to treat an infection or other cause of fluid build-up in the middle ear (14), these treatments may not immediately resolve the pain and discomfort caused by the buildup of fluid in the middle ear (14). The most immediate relief may be felt by the patient if the fluid can be removed from the ET (26).

Antibiotic treatment of middle ear infections may result in normal middle ear function within three to four weeks. During the healing period, the patient can experience varying degrees of ear pressure, popping, clicking and fluctuation of hearing, occasionally with shooting pain in the ear. Resolution of the infection may leave the patient with uninfected fluid in the middle ear (14), localized in the ET (26).

Fluid build-up caused by these types of infections may be treated surgically. The primary objective of surgical treatment of chronic serous otitis media may be to reestablish ventilation of the middle ear, keeping the hearing at a normal level and preventing recurrent infection that might damage the eardrum membrane and middle ear bones. One method to opening the ET (26) includes the "Valsalva" maneuver, accomplished by forcibly blowing air into the middle ear (14) while holding the nose, often called popping the ear. This method may be effective for opening the ET (26) but it may not clear the accumulated fluid from the middle ear (14) and is essentially a temporary fix when fluid is present in the middle ear (14).

Methods for treating the middle ear (14) and ET (26) include those disclosed in U.S. Patent Pub. No. 2010/0274188, entitled "Method and System for Treating Target Tissue within the ET," published on Oct. 28, 2010, now abandoned, the disclosure of which is incorporated by reference herein; U.S. Patent Pub. No. 2013/0274715, entitled "Method and System for Eustachian Tube Dilation," published on Oct. 17, 2013, now abandoned, the disclosure of which is incorporated by reference herein; and U.S. patent application Ser. No. 14/317,269, entitled "Vent Cap for a Eustachian Tube Dilation System," filed Jun. 27, 2014, published as U.S. Pat. No. 2015/0374963 on Dec. 31, 2015, the disclosure of which is incorporated by reference herein.

In some cases, the isthmus (29), which is the narrowest portion of the ET (26) at the junction of cartilaginous and bony portions of the middle ear (14), is clogged or otherwise constricted and thus prevents fluid communication between the ET (26) and the middle ear (14). Because the isthmus (29) is adjacent to sensitive middle ear (14) structures, precaution must be taken when treating the isthmus (29). It may therefore be desirable to provide methods and systems for accessing, diagnosing, and treating target tissue regions within or near the middle ear (14) and the ET (26), particularly within the isthmus (29).

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3A depicts a side elevational view of an exemplary guide catheter that may be used to position the dilation catheter of FIG. 5A.

FIG. 3B depicts a cross-sectional view of the guide catheter shown in FIG. 3A, taken along line 3B-3B of FIG. 3A.

FIG. 4 depicts an enlarged view of the distal end of the guide catheter shown in FIG. 3A.

FIG. 5A depicts a side elevational view of a balloon dilation catheter that may be used with the guide catheter of FIG. 3A.

FIG. 5B depicts a cross-sectional view of the balloon dilation catheter shown in FIG. 5A, taken along line 5B-5B of FIG. 6.

FIG. 6 depicts an enlarged view of the distal end of the balloon dilation catheter shown in FIG. 5A.

FIG. 12 depicts a side elevational view of the instrument of FIG. 11A inserted into a lumen of the balloon dilation catheter of FIG. 5A.

FIG. 12A depicts a detailed view of the distal end of the instrument of FIG. 11A inserted into a lumen of the balloon dilation catheter of FIG. 5A, as shown in FIG. 12.

FIG. 22 depicts a side elevational view of an exemplary instrument that may be used to treat a Eustachian tube isthmus via the balloon catheter of FIG. 5A, with an illumination element.

FIG. 22A depicts a detailed side elevational view of the distal end of the instrument of FIG. 22 inserted into a lumen of the balloon dilation catheter of FIG. 5A, as shown in FIG. 22.

DETAILED DESCRIPTION

Figure 1:
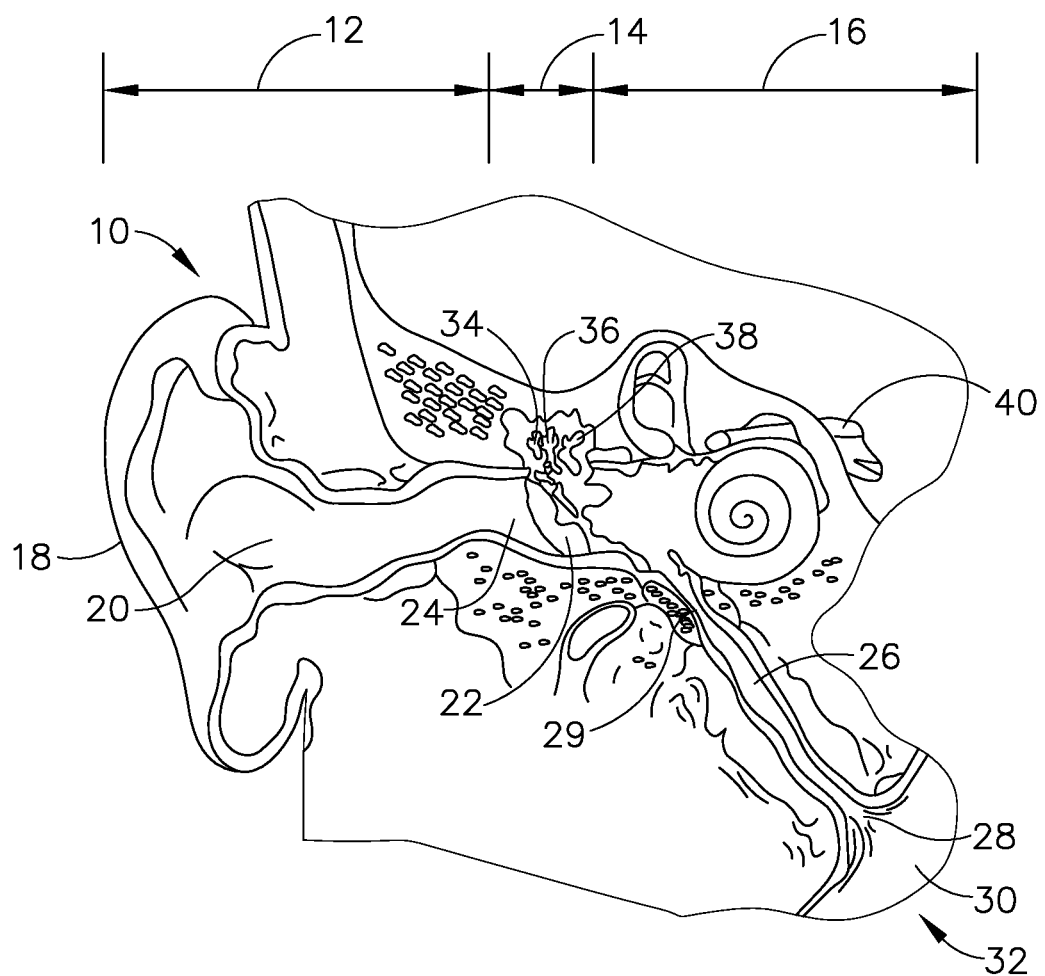
FIG. 1 depicts a cross-sectional view of a human ear showing the inner, middle and outer ear portions and the Eustachian tube connecting the middle ear with the nasopharynx region of the throat.
Figure 2:
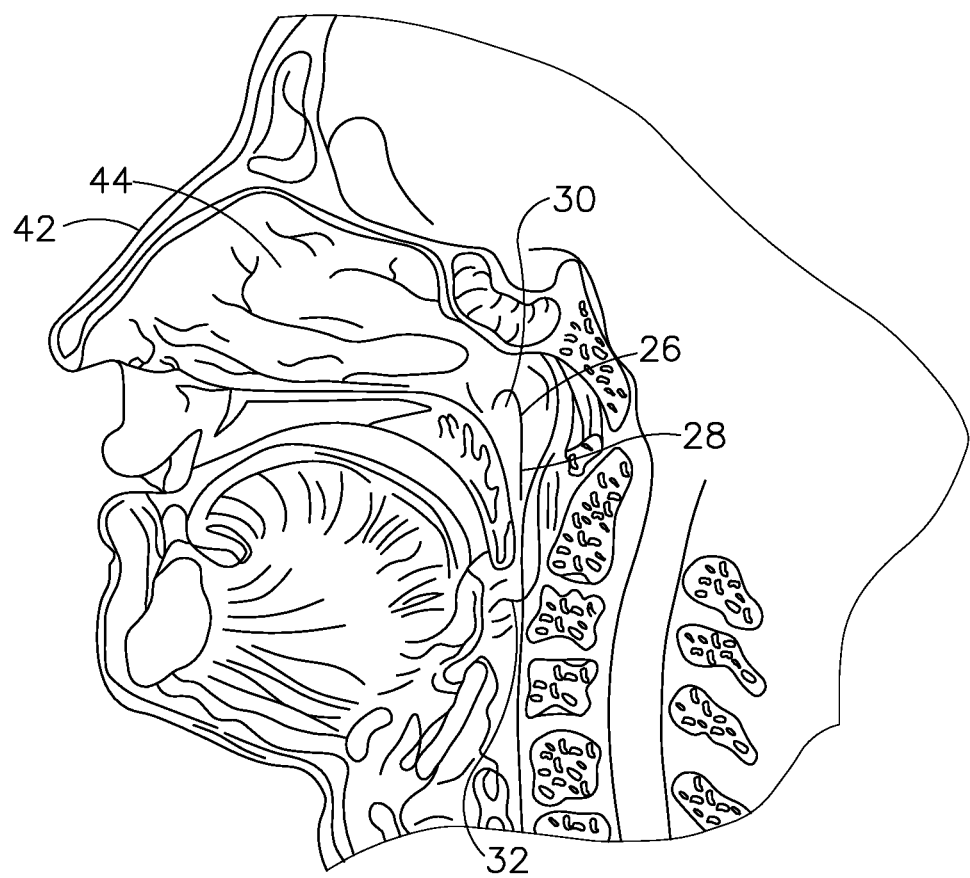
FIG. 2 depicts a cross-sectional view of a human head showing the nasopharynx region of the throat illustrated in FIG. 1 containing the pharyngeal ostium of the Eustachian tube illustrated in FIG. 1.

The following detailed description should be read with reference to the drawings, in which like elements in different drawings are identically numbered. The drawings, which are not necessarily to scale, depict exemplary examples for the purpose of explanation only and are not intended to limit the scope of the invention. The detailed description illustrates by way of example, not by way of limitation, the principles of the invention. This description will clearly enable one skilled in the art to make and use the invention, and describes several examples, adaptations, variations, alternative and uses of the invention, including what is presently believed to be the best mode of carrying out the invention.

As used herein, the terms "about" and "approximately" for any numerical values or ranges indicate a suitable dimensional tolerance that allows the part or collection of components to function for its intended purpose as described herein.

I. Exemplary Eustachian Tube Dilation Catheter System

One example of a treatment that may be performed to treat an ET (26) that does not provide sufficient communication between the middle ear (14) and the pharyngeal ostium (28) includes accessing and dilating the ET (26) using a guide catheter (100) and a balloon dilation catheter (200), examples of which are shown in FIGS. 3A-6. Guide catheter (100) of the present example includes an elongate tubular shaft (102) that has a proximal end (104), a distal end (106) and a lumen (108) therebetween. The guide catheter (100) may have any suitable length, diameter, angle of bend, and location of the bend along the length of the catheter (100), to facilitate accessing an ET (26) opening, such as the pharyngeal ostium (28). In some examples, the guide catheter (100) may have a length between about 8 cm and about 20 cm, or more particularly between about 10 cm and about 15 cm, or more particularly about 11 cm.

FIG. 3B is a cross-sectional view of the elongate tubular shaft (102) of guide catheter (100). As can be seen, shaft (102) has an outer shaft tube (110), an inner shaft tube (112) and a lumen (108). The outer shaft tube (110) may be constructed of a stiff material such as stainless steel and the inner shaft tube (112) may be constructed of a more flexible material such as a polymeric material including but not limited to nylon and further including a PTFE liner. The lumen (108) has a diameter of between about 2 mm and 3 mm, preferably between about 2.5 mm and about 2.6 mm, such that the balloon dilation catheter (200) can be easily inserted into the lumen (108) for dilation of the ET (26). The combination of guide catheter (100) and balloon catheter (200) may a compact system that is designed for a one-handed procedure. By "compact," it is intended that the length of the guide catheter shaft that is distal of the bend in the guide catheter is between about 0.5 and 2.0 about cm, in some versions between about 1 and about 2 cm, and in some versions about 1 cm. The compactness may help reduce interference with other instruments, such as an endoscope that may be used to help in visualizing the positioning of the system, as described below.

The distal portion (120) of guide catheter (100) is shown in an enlarged view in FIG. 4. The distal portion (120) of the guide catheter (100) may have a bend (122) with an angle between about 45 degrees and about 65 degrees, and more preferably between about 50 degrees and about 60 degrees, and particularly about 55 degrees, to facilitate access into the ET (26) via the pharyngeal ostium (28). The distal portion (120) of the guide catheter (100) is made of a transparent material such as a polymer including but not limited to nylon and PTFE such that balloon dilation catheter (200) is visible within the distal portion (120) and such that distal portion (120) is more flexible than the elongate shaft (102). The distal tip (124) of the distal portion (120) of the guide catheter (100) is made of PEBAX® (polyether block amide) such that it provides for atraumatic access to the ET (26), and may contain 20% barium sulfate or other similar radiopaque materials for visualizable access.

Referring again to FIG. 3A, the proximal portion (130) of guide catheter (100) includes a proximal hub (132) to aid in insertion of the balloon catheter into the ET (26). The hub (132) has a larger diameter proximal end (134) and a smaller diameter middle section (136) to facilitate stabilization of the guide catheter (100) in the nose, rotation of the guide catheter (100), and insertion of the balloon catheter (200) as will be described in further detail below. The hub (132) is ergonomically designed for insertion, location, and rotation through slight manipulations with one hand.

Balloon dilation catheter (200) of the present example is shown in FIG. 5A. The balloon dilation catheter (200) of the present example generally includes an elongate shaft (202) having a proximal end (214) and a distal end (218). The balloon dilation catheter (200) further includes a balloon (204) on the distal end (218) of the elongate shaft (202). The balloon (204) may be a polymer balloon (compliant, semi-compliant, or non-compliant). In some versions, the balloon (204) comprises a suitable non-compliant material such as but not limited to polyethylene terephthalate (PET), PEBAX® (polyether block amide), nylon or the like. The balloon catheter (200) may include any size of balloon including, but not limited to, balloons of 2 mm to 8 mm in diameter or of between about 5 mm and 6 mm (when inflated) and 12 mm to 24 mm in working length (for example 2 mm×12 mm, 3.5 mm×12 mm, 5 mm×16 mm, 5 mm×24 mm, 6 mm×16 mm, 6 mm×20 mm, 6 mm×24 mm, 7 mm×16 mm and 7 mm×24 mm) The balloon dilation catheter (200) generally includes a proximally located connection (230) for inflating/activating the balloon (204) by communicating a pressurized medium (e.g., saline) to balloon (204).

Figure 9:
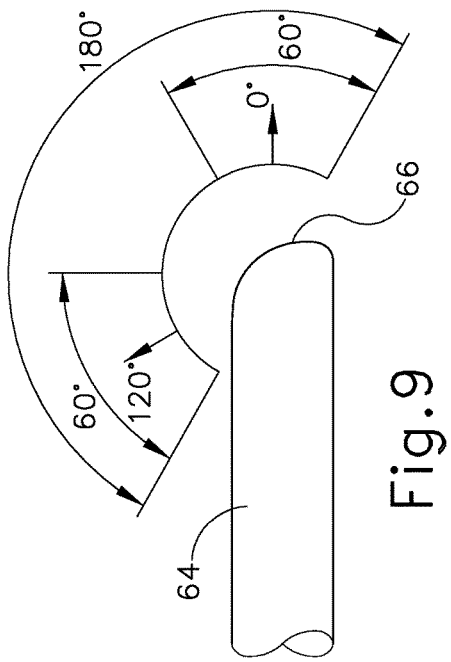
FIG. 9 depicts a side elevational view of the distal end of the endoscope of FIG. 8, showing an exemplary range of viewing angles.
Figure 10A:
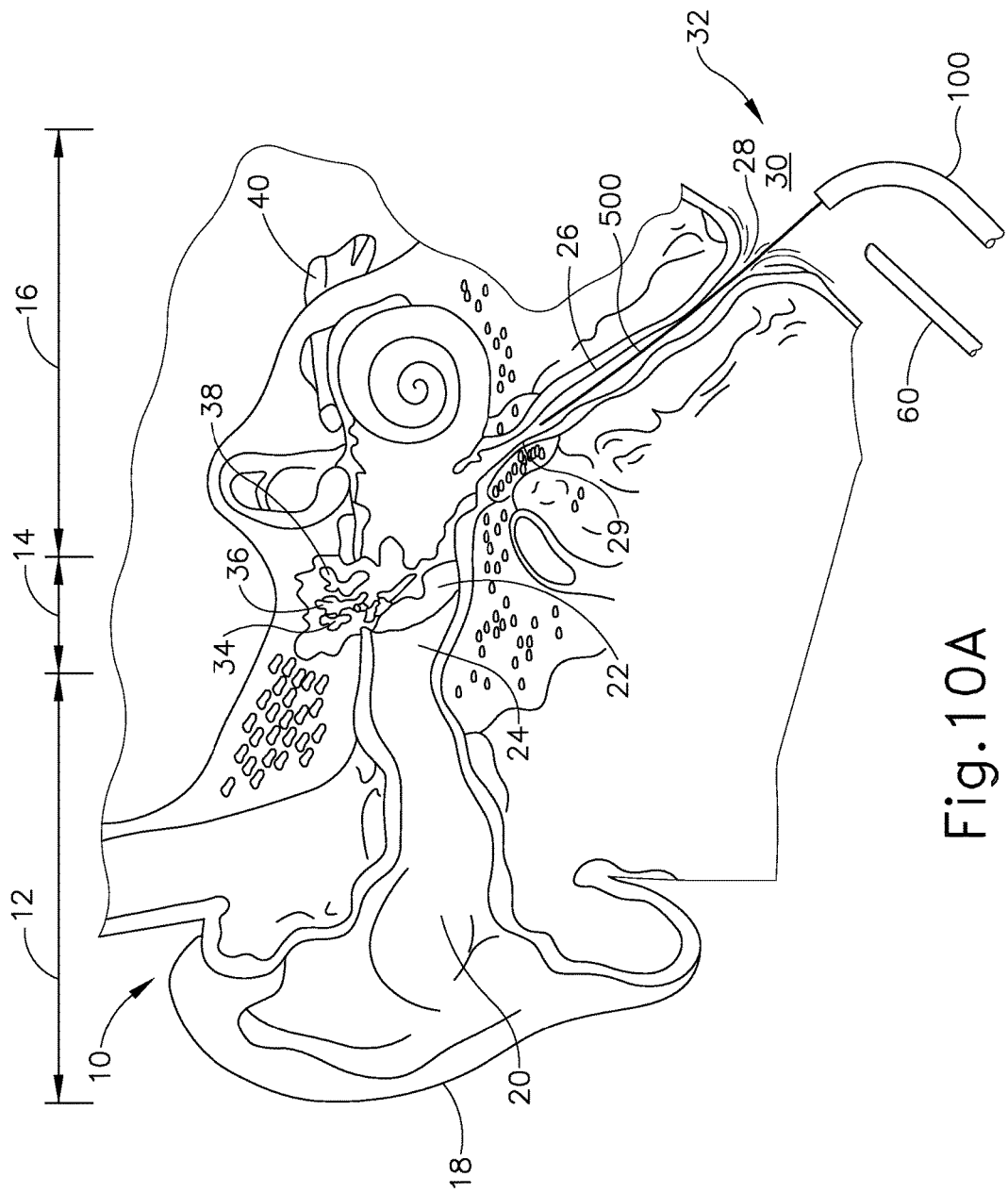
FIG. 10A depicts a cross-sectional view of a guide catheter, a balloon catheter, and an endoscope being positioned in relation to a Eustachian tube of a patient, with a guidewire disposed in the Eustachian tube.
Figure 10B:
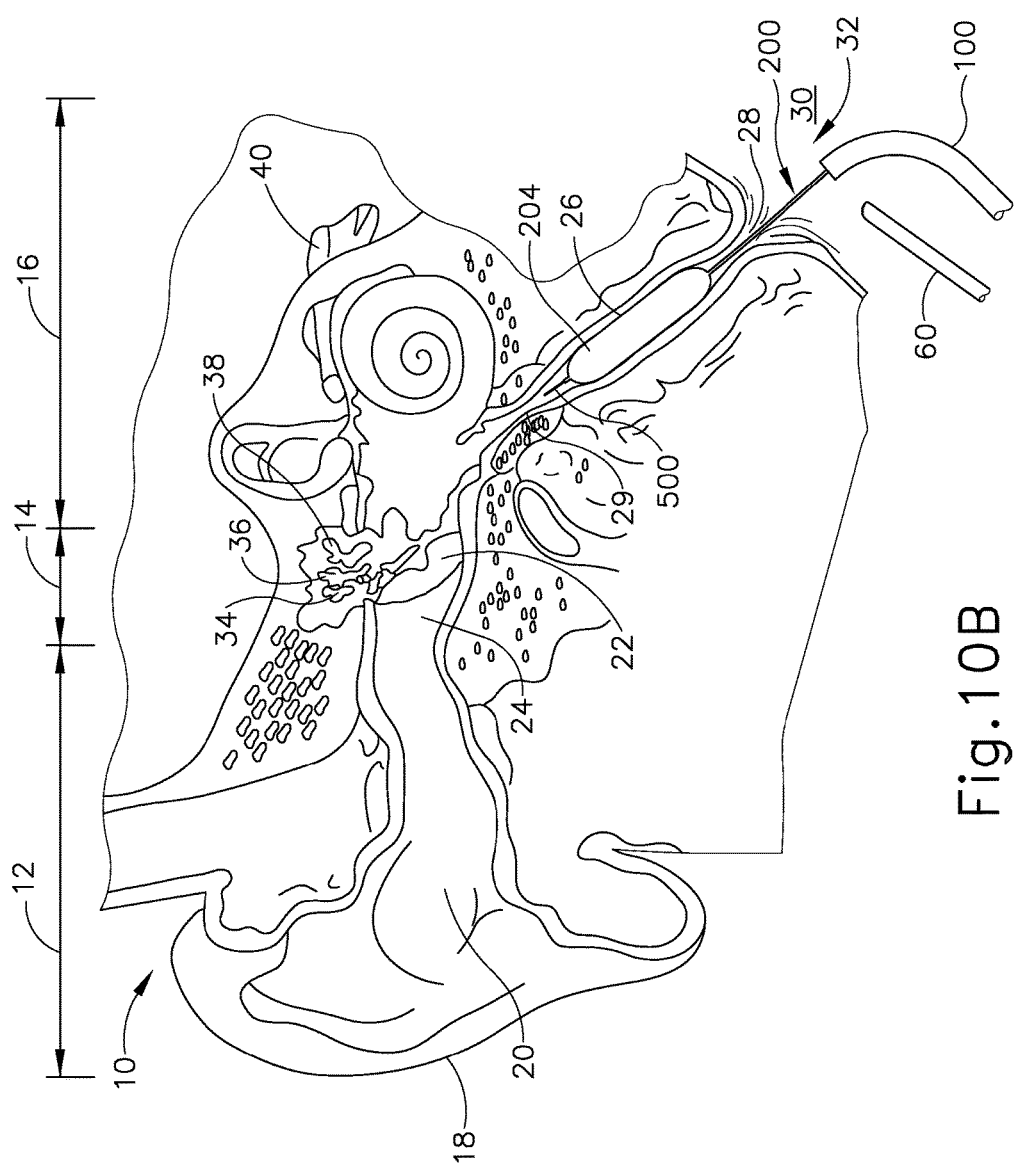
FIG. 10B depicts a cross-sectional view of the guide catheter, balloon catheter, and endoscope of FIG. 10A, with a balloon of the balloon catheter being expanded to dilate the Eustachian tube.

Balloon (204) may be expanded to dilate the ET (26) after balloon (204) is placed in a desirable location in the ET (26), as shown in FIGS. 10A-10B and described in greater detail below. For example, the opening area of the ET (26) includes a pharyngeal ostium (28), and dilation catheter (200) may be advanced to position the balloon in the pharyngeal ostium (28). An endoscope, such as endoscope (60) (FIGS. 8-9), may be used to assist in positioning the dilation catheter (200). Endoscope (60) may be advanced through the nasal passage to view the dilation catheter (200). A marker (208) on a shaft of the dilation catheter (200) can be viewed from endoscope (60) to approximate a location of the balloon (204) relative to the opening of the ET (26) (e.g., pharyngeal ostium (28)) based on a distance of the marker (208) from a proximal end of the balloon (204). Accordingly, dilation catheter (200) can be moved to place marker (208) in a desirable location before expansion of the balloon (204) in the ET (26).

Balloon dilation catheter (200) further includes an actuator (210). Actuator (210) has a proximal side 220 and a distal side (222). In the example shown in FIG. 5A, actuator (210) is secured by an adhesive to elongate shaft (202). The portion (240) of elongate shaft (202) that is distal of actuator (210) is sufficiently stiff to be guided through the nasal cavity and into the ET (26) and is constructed of stainless steel and preferably includes a stainless steel hypotube. The portion (238) of elongate shaft (202) that is proximal of actuator (210) and the portion (250) that is distal to portion (240) is more flexible than the portion (240) and is constructed of a polymeric material including but not limited to PEBAX® (polyether block amide). In this way, proximal portion (238) of elongate shaft (202) will not interfere with the endoscope (60) described above as it is advanced through the nasal passage, such that the dilation catheter (200) can be easily viewed. The actuator (210) allows for easy, ergonomic one-handed advancement of dilation catheter (200) through guide catheter (100) and into the ET (26). Actuator (210) may be used to advance or retract in alternative ways including but not limited to use of the thumb, the index finger, or a combination of fingers (e.g., the index and middle fingers) or the thumb and the index or middle finger.

The distal end (218) of balloon catheter (200) further includes a tip (212) and a flexible shaft portion (250) that is constructed of a polymeric material including but not limited to PEBAX® (polyether block amide) that extends from the distal end of the elongate shaft (202) to the proximal end of balloon (204). In the example shown in FIG. 5A, tip (212) is a bulbous polymeric blueberry shaped, atraumatic tip and is about 1.5 mm to about 2 mm in length, with an outer diameter of between about 2 mm and about 3 mm. The smoothness and roundness of tip (212) facilitates advancement of the balloon catheter (200) by helping it glide smoothly through the ET (26). Tip (212) further acts as a safety stop. The isthmus (29) of the ET (26), shown in FIG. 1 is approximately 1 mm in diameter. The tip (212) diameter is larger than the outer diameter (233) of the elongate shaft (202) shown in cross-section in FIG. 5B such that the tip (212) size will prevent the balloon catheter (200) from passing through the isthmus (29) into the middle ear (14).

After balloon (204) is positioned within the ET (26) and inflated to an expanded state (e.g., as shown in FIG. 10B), balloon (204) may be held in location while in an expanded state for an extended period of time (e.g. several seconds or minutes). The balloon catheter (200) may also deliver a substance to the ET (26), such as one or more of the therapeutic or diagnostic agents described herein. Balloon (204) may also carry an expandable stent for delivery into the ET (26) upon expansion of balloon (204). Balloon dilation catheter (200) and guide catheter (100) may be removed from the patient after balloon (204) has been deflated/unexpanded. The ET (26) will resume functioning, normally opening and closing to equalize atmospheric pressure in the middle ear (14) and protect the middle ear (14) from unwanted pressure fluctuations and loud sounds.

Figure 7:
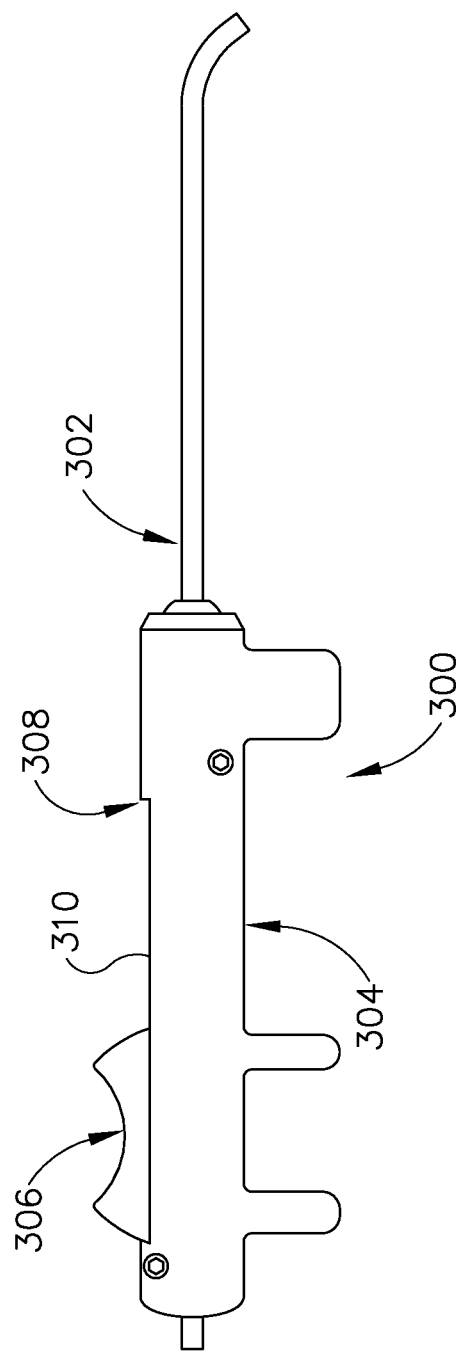
FIG. 7 depicts a side elevational view of another exemplary guide catheter that may be used to position the dilation catheter of FIG. 5A.

Another exemplary guide catheter (300) is shown in FIG. 7. In this example, proximal hub (132) is replaced with a handle (304). Guide catheter (300) comprises an elongate shaft (302) and a handle (304) to aid in insertion of a balloon catheter, such as balloon catheter (200), into the ET (26) in a manner similar to that described below with regard to the guide catheter (200). In the example shown in FIG. 7, an actuator (306) in the form of a slider is attached to portion of balloon catheter (200) that is contained within handle (304) and is slidably contained within elongate shaft (302) of guide catheter (300). Actuator (306) is thus slidable relative to handle (304) along a channel (310) to thereby selectively advance and retract balloon catheter (200) relative to elongate shaft (302). In use, elongate shaft (302) is inserted into the paranasal cavity of the patient and balloon catheter (200) is advanced into the ET (26) via thumb or single finger advancement of actuator (302) along channel (310) of handle (304). The advancement of balloon catheter (200) is continued until a visual marker indicates that advancement is complete, or until the enlarged tip (212) of balloon catheter (200) abuts the isthmus of the ET (26); or actuator (302) abuts the distal end (308) of channel (310) in handle (304) and is therefore fully deployed.

II. Exemplary Endoscope

Figure 8:
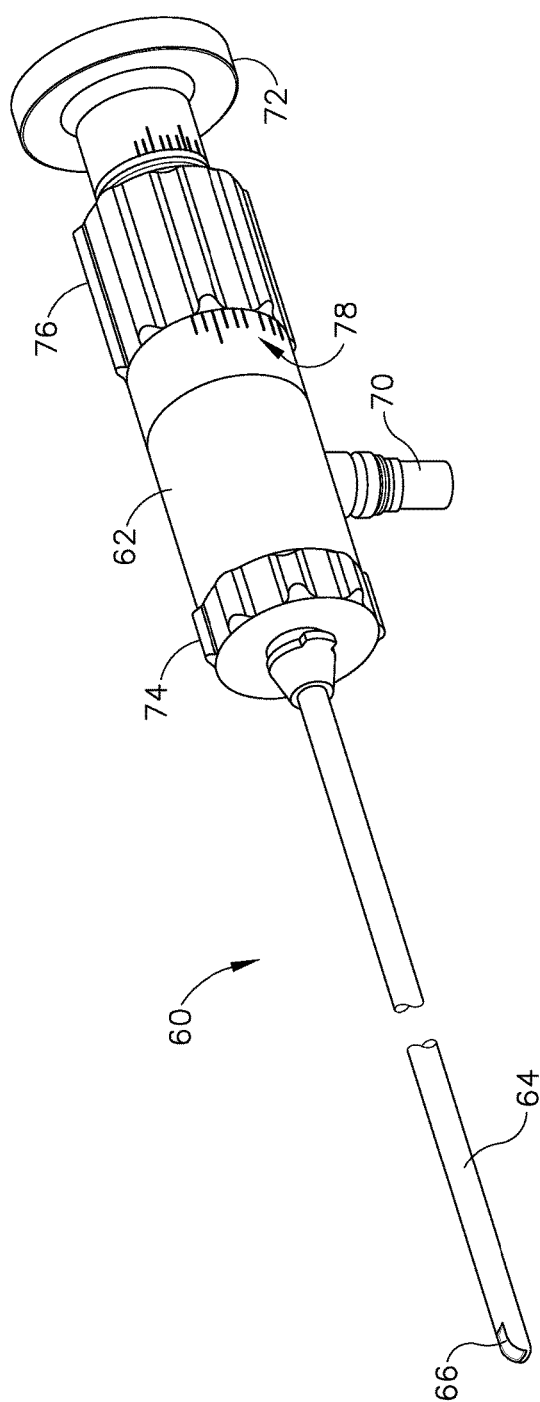
FIG. 8 depicts a perspective view of an exemplary endoscope suitable for use with the guide catheter of FIG. 3A and/or the balloon dilation catheter of FIG. 5A.

Referring to FIGS. 8-9, an endoscope (60) may be used to provide visualization within an anatomical passageway (e.g., within the oro-nasal cavity, etc.) during the process using guide catheter (100) and/or balloon catheter (200) just described, for example. Endoscope (62) of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

As noted above, an endoscope (60) may be used to provide visualization within an anatomical passageway (e.g., within the nasal cavity, etc.) during a process of using dilation catheter system, which in one example includes the balloon dilation catheter (200, 300) and, optionally, guide catheter (100). As shown in FIGS. 8-9, endoscope (60) of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, now abandoned, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein III. Exemplary Method of Treating the Eustachian Tube FIGS. 10A-10B show schematic versions of the guide catheter (100) and balloon catheter (200) being used to treat the ET (26) under visual guidance using endoscope (60). In use, guide catheter (100) may be advanced into a nostril and through a nasal cavity to position a distal end of the catheter (100) at, in or near the pharyngeal ostium (28), which opens into the ET (26). In some instances, the guide catheter (100) may be passed through a nostril to the ET (26) on the ipsilateral (same side) of the head. In some other instances, the guide catheter (100) may be passed through a nostril to the ET (26) on the contralateral (opposite side) of the head. A guiding element such as a guidewire (500) or illuminating fiber may be used to aid in accessing the ET (26). In some versions, guidewire (500) is omitted.

As shown in FIG. 10B, after guide catheter (100) is in a desired position, balloon catheter (200) is advanced through the guide catheter (100) to position balloon (204) of balloon catheter (200) within the ET (26). The physician/user may place the index and middle fingers on either side of the smaller diameter middle section (136) of proximal hub (132) of guide catheter (100). The physician/user will then place the thumb on the proximal side (220) of actuator (210) or within both sides of the actuator (210) and will use the thumb to slide the balloon dilation catheter (200) through guide catheter (100) to position balloon (204) within the ET (26). Alternatively, the user may grasp proximal hub (132) of guide catheter (100) and use the index finger placed on the proximal side (220) of actuator (210) or in between the distal side (222) and the proximal side (220) of actuator (210) to advance balloon catheter (200). The larger diameter tip (212) prevents balloon catheter (200) from advancing past the isthmus (29) and into the middle ear (14). Further, distal side (222) of actuator (210) will bottom out against proximal end (104) of guide catheter (100), such that the balloon catheter (200) cannot advance any further. The actuator (210) thus prevents the balloon catheter (200) from reaching passing the isthmus (29) and reaching the middle ear (14). Further, actuator (210) can be positioned at the appropriate distance along the elongate shaft (202) such that access to the ET (26) may be from the contralateral or the ipsilateral side.

In an alternative example, a balloon catheter (200) is advanced into a nostril of a patient without the use of a guide catheter (100). The balloon (204) of the balloon catheter (200) is placed within the ET (26). The physician/user will advance the balloon catheter (200) until the proximal side (220) of the actuator (210) is adjacent the patient's nostril. The distal side (222) of the actuator (210) will bottom out against the patient's nostril, such that the balloon catheter cannot advance any further. The actuator (210) prevents the catheter from passing the isthmus (29) and reaching the middle ear (14). Further, actuator (210) can be positioned at the appropriate distance along the elongate shaft (202) such that access to the ET (26) may be from the contralateral or the ipsilateral side.

Any number of procedures may be carried out following placement of the balloon catheter (200) into the desired position as described above. For instance, the Eustachian tube (ET) may be dilated by communicating fluid to balloon (204) and thereby inflating balloon (204), in accordance with the teachings of various reference cited herein or otherwise. In addition or in the alternative, the isthmus (29) may be cleaned and/or otherwise treated as described in greater detail below.

The elongate shaft (202) contains adjacent dual lumen (232, 234) tubing (see FIG. 5B). By adjacent dual lumen tubing, it is intended that the lumens (232, 234) are next to each other but are spaced apart, one from the other. The inflation lumen (232) is used for inflation of the balloon (204) with water, contrast medium, or saline through inflation port (230) to a pressure of between about 3 and about 15 atmospheres, or of between about 6 and about 12 atmospheres. The injection lumen (234) permits the optional injection of water, medicament, or even the introduction of a guidewire (500) through the injection port (236) at the proximal end (216) of the proximal connector (206). In order to ensure that inflation port (230) is used for balloon (204) inflation only, inflation port (230) and injection port (236) may optionally have different type connectors. For example, inflation port (230) may be a female connector whereas injection port (236) is a male connector or vice versa. Alternatively, injection port (236) may have a right-handed thread connector and inflation port (230) may have a left-handed thread connector or vice versa. It may be desirable to inject solutions containing contrast agents, pharmaceutically acceptable salt or dosage form of an antimicrobial agent (e.g. antibiotic, antiviral, anti-parasitic, antifungal, etc.), an anesthetic agent with or without a vasoconstriction agent (e.g. Xylocaine with or without epinephrine, Tetracaine with or without epinephrine, etc.), an analgesic agent, a corticosteroid or other anti-inflammatory (e.g. an NSAID), a decongestant (e.g. vasoconstrictor), a mucus thinning agent (e.g. an expectorant or mucolytic), a surfactant, an agent that prevents or modifies an allergic response (e.g. an antihistamine, cytokine inhibitor, leucotriene inhibitor, IgE inhibitor, immunomodulator), an allergen or another substance that causes secretion of mucous by tissues, hemostatic agents to stop bleeding, antiproliferative agents, cytotoxic agents (e.g. alcohol), biological agents such as protein molecules, stem cells, genes or gene therapy preparations, or the like.

Some nonlimiting examples of antimicrobial agents that may be used in this invention include acyclovir, amantadine, aminoglycosides (e.g., amikacin, gentamicin and tobramycin), amoxicillin, amoxicillinlclavulanate, amphotericin B, ampicillin, ampicillinlsulbactam, atovaquone, azithromycin, cefazolin, cefepime, cefotaxime, cefotetan, cefpodoxime, ceflazidime, ceflizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscarnet, ganciclovir, atifloxacin, imipenemlcilastatin, isoniazid, itraconazole, ketoconazole, metronidazole, nafcillin, nafcillin, nystatin, penicillin, penicillin G, pentamidine, pip eracillinitazobactam, rifampin, quinupristindalfopristin, ticarcillinl-clavulanate, trimethoprimlsulfamethoxazole, valacyclovir, vancomycin, mafenide, silver sulfadiazine, mupirocin (e.g., Bactroban, Glaxo SmithKline, Research Triangle Park, N.C.), nystatin, triamcinolonelnystatin, clotrimazolelbetamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulphonated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as "plantibodies;" agents which change the condition of the tissue to make it hostile to the pathogen (such as substances which alter mucosal pH (e.g., Buffer Gel and Acid form); non-pathogenic or "friendly" microbes that cause the production of hydrogen peroxide or other substances that kill or inhibit the growth of pathogenic microbes (e.g., lactobacillus); antimicrobial proteins or peptides such as those described in U.S. Pat. No. 6,716,813 (Lin et al.,) which is expressly incorporated herein by reference or antimicrobial metals (e.g., colloidal silver).

Additionally or alternatively, in some applications where it is desired to treat or prevent inflammation the substances delivered in this invention may include various steroids or other anti-inflammatory agents (e.g., nonsteroidal anti-inflammatory agents or NSAIDS), analgesic agents or antipyretic agents. For example, corticosteroids that have previously administered by intranasal 10 administration may be used, such as beclomethasone (Vancenase® or Beconase), flunisolide (Nasalid®), fluticasone proprionate (Flonase®), triamcinolone acetonide (Nasacort®), budesonide (Rhinocort Aqua®), loterednol etabonate (Locort) and mometasone (Nasonex®). Other salt forms of the aforementioned corticosteroids may also be used. Also, other non-limiting examples of steroids that may be useable in the present invention include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexarnethasone and methylprednisolone. Other anti-inflammatory, analgesic or antipyretic agents that may be used include the nonselective COX inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2 Inhibitors (e.g., diaryl-substituted furanones such as rofecoxib; diaryl-substituted pyrazoles such as celecoxib; indole acetic acids such as etodolac and sulfonanilides such as mmesulide).

Additionally or alternatively, in some applications, such as those where it is desired to treat or prevent an allergic or immune response and/or cellular proliferation, the substances delivered in this invention may include a) various cytokine inhibitors such as humanized anti-cytokine antibodies, anti-cytokine receptor antibodies, recombinant (new cell resulting from genetic recombination) antagonists, or soluble receptors; b) various leucotriene modifiers such as zafirlukast, montelukast and zileuton; c) immunoglobulin E (IgE) inhibitors such as Omalizumab (an anti-IgE monoclonal antibody formerly called rhu Mab-E25) and secretory leukocyte protease inhibitor) and d) SYK Kinase inhibitors such as an agent designated as "R-112," manufactured by Rigel Pharmaceuticals, Inc, South San Francisco, Calif.

Additionally or alternatively, in some applications, such as those where it is desired to shrink mucosal tissue, cause decongestion, or effect hemostasis, the substances delivered in this invention may include various vasoconstrictors for decongestant and or hemostatic purposes including but not limited to pseudoephedrine, xylometazoline, oxymetazoline, phenylephrine, epinephrine, etc.

Additionally or alternatively, in some applications, such as those where it is desired to facilitate the flow of mucous, the substances delivered in this invention may include various mucolytics or other agents that modify the viscosity or consistency of mucous or mucoid secretions, including but not limited to acetylcysteine. In one particular example, the substance delivered by this invention comprises a combination of an anti-inflammatory agent (e.g. a steroid or an NSAID) and a mucolytic agent.

Additionally or alternatively, in some applications such as those where it is desired to prevent or deter histamine release, the substances delivered in this invention may include various mast cell stabilizers or drugs which prevent the release of histamine such as cromolyn (e.g., Nasal Chroma) and nedocromil.

Additionally or alternatively, in some applications such as those where it is desired to prevent or inhibit the effect of histamine, the substances delivered in this invention may include various antihistamines such as azelastine (e.g., Astylin) diphenhydramine, loratidine, etc.

Additionally or alternatively, in some examples such as those where it is desired to dissolve, degrade, cut, break or remodel bone or cartilage, the substances delivered in this invention may include substances that weaken or modify bone and/or cartilage to facilitate other procedures of this invention wherein bone or cartilage is remodeled, reshaped, broken or removed. One example of such an agent would be a calcium chelator such as EDTA that could be injected or delivered in a substance delivery implant next to a region of bone that is to be remodeled or modified. Another example would be a preparation consisting of or containing bone degrading cells such as osteoclasts. Other examples would include various enzymes of material that may soften or break down components of bone or cartilage such as collagenase (CGN), trypsin, trypsinlLEDTA, hyaluronidase, and tosyllysylchloromethane (TLCM).

Additionally or alternatively, in some applications such as those wherein it is desired to treat a tumor or cancerous lesion, the substances delivered in this invention may include antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other antitumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-I, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, 1MC-IC11, 1M862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, bacillus calmetteguerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogslcongeners and derivatives of such compounds as well as other antitumor agents not listed here.

Additionally or alternatively, in some applications such as those where it is desired to grow new cells or to modify existing cells, the substances delivered in this invention may include cells (mucosal cells, fibroblasts, stem cells or genetically engineered cells) as well as genes and gene delivery vehicles like plasmids, adenoviral vectors or naked DNA, mRNA, etc. injected with genes that code for anti-inflammatory substances, etc., and, as mentioned above, osteoclasts that modify or soften bone when so desired, cells that participate in or effect mucogenesis or ciliagenesis, etc.

In one example, a local anesthetic, such as Lidocaine is injected through the injection lumen (234) prior to dilation of the ET (26). The injection lumen (234) can be used for venting during dilation so that pressure in the middle ear (14) does not increase or decrease.

IV. Exemplary Instrument for Treating the Isthmus of the Eustachian Tube

On some occasions, issues with the ET (26) may be caused by an isthmus (29) that is clogged by debris or is otherwise obstructed, thereby preventing proper functioning of the ET (26), i.e., opening and closing to relieve pressure in the middle ear (14), for example. In some such instances, simply dilating the ET (26) as described herein may be insufficient to treat middle ear (14) and other issues. It may therefore be desirable to provide an instrument that is capable of clearing the isthmus (29) without creating a risk of trauma to structures in the middle ear (14). Any attempt to clean the isthmus (29) ought to be taken with extreme care due to the proximity of the isthmus (29) to sensitive middle and inner ear (14, 16) anatomy. The isthmus (29) may be cleared before, during, or after a procedure in which the ET (26) is dilated. In some instances, the isthmus (29) may be cleared without dilating the ET (26) at all. Several examples of instruments that may be used to clear the isthmus (29) will be described in greater detail below, while other examples will be apparent to those of ordinary skill in the art in view of the teachings herein.

Figure 11A:
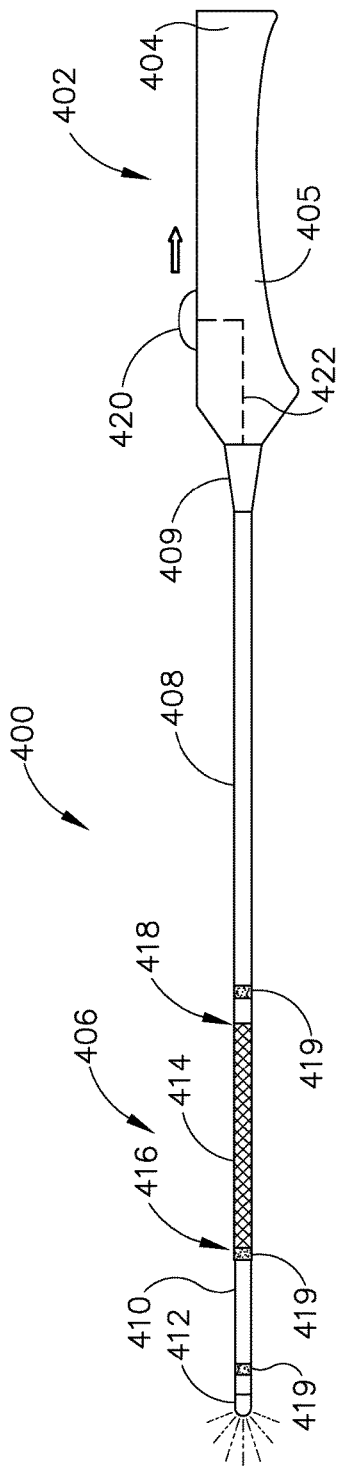
FIG. 11A depicts a side elevational view of an exemplary instrument that may be used to treat a Eustachian tube isthmus via the balloon catheter of FIG. 5A, with an expandable element of the instrument in a contracted configuration.
Figure 11B:
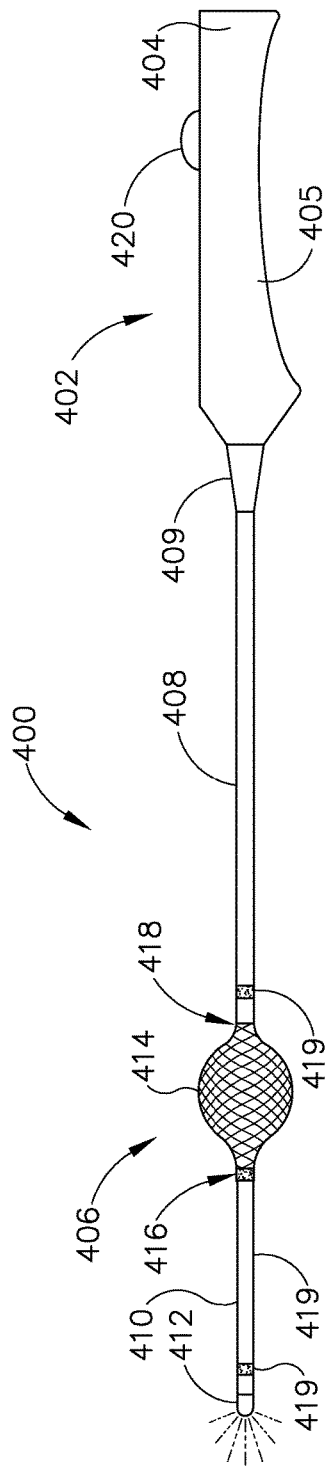
FIG. 11B depicts a side plan elevational of the instrument of FIG. 11A, with the expandable element in an expanded configuration.

FIGS. 11A-B show an exemplary instrument (400) that may be used to clear the isthmus (29) of an ET (26). Instrument (400) may be used in combination with a variety of guide devices and other devices, such as, for example, guide catheter (100, 300) and balloon dilation catheter (200), in order to traverse the oro-nasal cavity and access the ET (26) and isthmus (29). In the present example, instrument (400) includes a proximal portion (402) with a handle (404) that may be grasped by a user. Handle (404) includes a curved portion (405) to better fit a user's fingers or other parts of the hand, to increase the overall ergonomics of instrument (400). Instrument (400) includes a distal portion (406) and a shaft (408) extending between the proximal and distal portions (402, 406). In the example shown, at least a portion of shaft (408) is flexible in order to traverse the anatomy of the oro-nasal cavity, guide catheter (100), and/or balloon catheter (200), for example. Instrument (400) includes a tapered transition portion (409) between handle (404) and shaft (408).

Distal portion (406) includes a distal shaft (410) having a tip (412). In the present example, tip (412) includes an atraumatic, rounded end and is configured and sized to pass through isthmus (29). Tip (412) is further configured to prevent damage to structures within the middle ear (14) and other portions of the oro-nasal cavity as it instrument (400) traverses the anatomy. Moreover, tip (412) of the present example may include a light source in order to illuminate the ET (26) or another anatomy to determine, for example, whether the isthmus (29) is clogged or otherwise obstructed. By way of example only, the light source may comprise an LED embedded in tip (412). In some such versions, wires or other electrical conduits may extend along shaft (408) to provide electrical power to the LED. As another merely illustrative example, the light source may be provided by an optically transmissive element at the distal end of one or more optical fibers that extend along the length of shaft (408). Other suitable forms that the light source may take will be apparent to those of ordinary skill in the art in view of the teachings herein.

As shown, distal shaft (410) includes a smaller outer cross-sectional dimension (e.g., diameter) than an outer cross-sectional dimension of shaft (408). Distal portion (406) includes an expandable element (414) that, in the example shown, comprises a metal braided mesh structure (e.g., stainless steel) disposed over distal shaft (410). In other examples, expandable element (414) may comprise other materials such as plastic or other polymers, or may be a combination of metal and other materials. Moreover, in other examples, expandable element (414) may have other types of mesh configurations. Expandable element (414) is shown in an unexpanded or contracted configuration in FIG. 11A and an expanded configuration in FIG. 11B. Expandable element (414) may be configured such it has a lower coefficient of friction in the unexpanded configuration than in the expanded configuration, to allow instrument (400) to traverse through lumen (234) of balloon catheter (200) in the unexpanded configuration, for example, and to better enable cleaning of the isthmus (29) in the expanded configuration, as discussed in more detail below.

In the present example, referring also to FIGS. 12 and 12A, at least the portions of device distal to transition portion (409) are sized and configured to be received within lumen (234) of balloon catheter (200). Moreover, instrument (400) is sized and configured such that when transition portion (409) is received within proximal connector (206) of balloon catheter (200), at least the expandable element (414) protrudes from the distal end of balloon catheter (200), shown best in FIG. 12A. Moreover, in some versions, transition portion (409) is configured to friction fit within the proximal end (216) of proximal connector (206). In some versions, transition portion (409) and/or proximal end (216) of proximal connector (206) may include a frictional coating or treatment that increases the frictional force between transition portion (409) and proximal connector (206). Friction between the transition portion (409) and proximal connector (206) may prevent relative movement between the balloon catheter (200) and instrument (400) when they are being directed together into the oro-nasal cavity to treat the ET (26) and isthmus (29), as discussed in more detail below. In the example shown, instrument (400) is configured to be front loaded into proximal connector (206) of balloon catheter (200). In other words, distal portion (406) of instrument (400) may be directed into proximal connector (206) and lumen (234) of balloon catheter (200) until at least the expandable element (414) and distal shaft (410) protrude from the distal end (218) of balloon catheter (200).

In some examples, instrument (400) is loaded into the balloon catheter (200) prior to the insertion of balloon catheter (200) into the anatomy, such that the instrument (400) and balloon catheter (200) may traverse the anatomy as a unit. However, in other examples, instrument (400) may be directed into balloon catheter (200) as described herein after balloon catheter (200) has already been directed into the anatomy (e.g., oro-nasal cavity), and perhaps even after balloon catheter has been used to dilate an anatomical region (e.g., the ET (26)). In further examples, instrument (400) may be configured to be backloaded into balloon catheter (200). In those examples, a modified distal end (not shown) of instrument (400) would be directed into distal end (218) of balloon catheter (200) until the configuration of the balloon catheter (200) and instrument (400) shown in FIG. 12A is reached. In some examples, balloon catheter (200) and instrument (400) may be configured such that when balloon (404) is positioned to dilate the ET (26), expandable element (414) is positioned adjacent to or coincident with the isthmus (29).

In the present example, instrument (400) includes a plurality of markers (419) that may be visualized directly, via an endoscope, or via an imaging device (e.g., fluoroscopy), to determine the position of the instrument (400) relative to certain portions of the anatomy (e.g., ET (26), isthmus (29), etc) or other devices within the anatomy (e.g., guide catheter (100), balloon catheter (200), etc.). As shown, instrument (400) has three markers (419), one being on distal shaft (410), another being on distal end (416) of expandable member (414), and another being on shaft (408). However, it will be understood that there may be more or less markers (419) than shown, and that markers (419) may be positioned differently than shown.

In order to transition to the expanded configuration, in the present example, a distal end (416) of expandable element (414) moves proximally while a proximal end (418) of expandable element (414) remains stationary. More particularly, handle (404) includes an actuator (420) that is in communication with expandable element (414). For example, actuator (420) may be in communication with distal end (416) of expandable element (414) via an elongate element (422) (shown in hidden lines in FIG. 11A). By way of example only, elongate element (422) may comprise a push-pull cable, a rod, a band, and/or various other kinds of structures that are capable of communicating longitudinal movement. As shown in the present example, actuator (420) is moved in a proximal direction in order to transition expandable element (414) to the expanded configuration. The actuator (420) may then be moved in the distal direction back to the position shown in FIG. 11A to transition expandable element (414) back to the unexpanded configuration. In other examples, actuator (420) may be configured in an opposite manner, i.e., distal movement of actuator (420) may result in the expansion of expandable element (414) while proximal movement of actuator (420) may result in contraction of expandable element (414). In further examples, actuator (420) does not move linearly. For instance, actuator (420) may instead be configured to move rotationally; in a combination of rotational, linear, or other movements; and/or in some other fashion in order to transition the expandable element (414) between the expanded and unexpanded configurations. Other alternative manners of transitioning expandable element (414) between the expanded and unexpanded configurations are possible and will be apparent to those of ordinary skill in the art in view of the teachings herein.

Figure 13A:
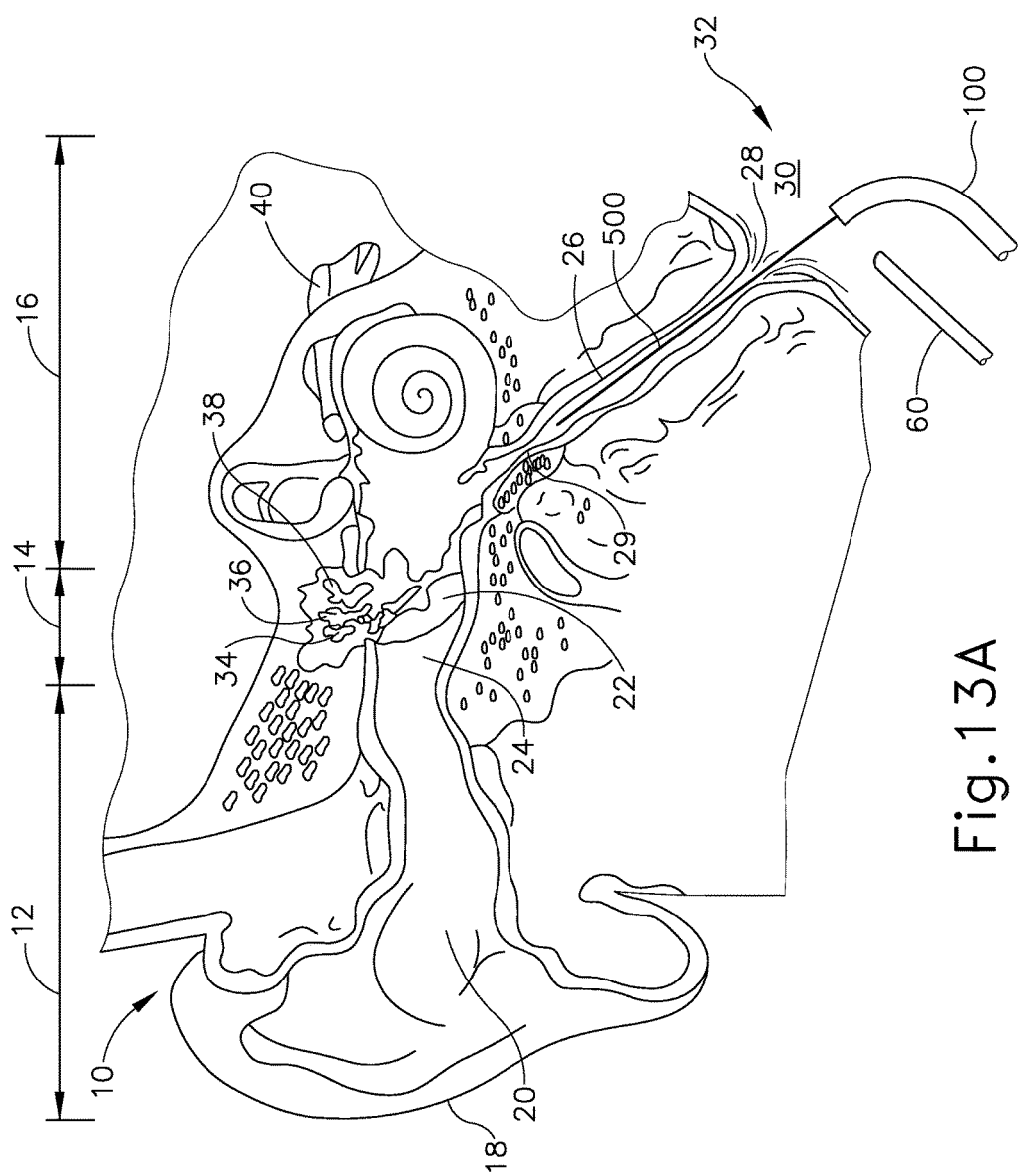
FIG. 13A depicts a cross-sectional view of a guide catheter and an endoscope being positioned in relation to a Eustachian tube of a patient, with a guidewire disposed in the Eustachian tube.
Figure 13B:
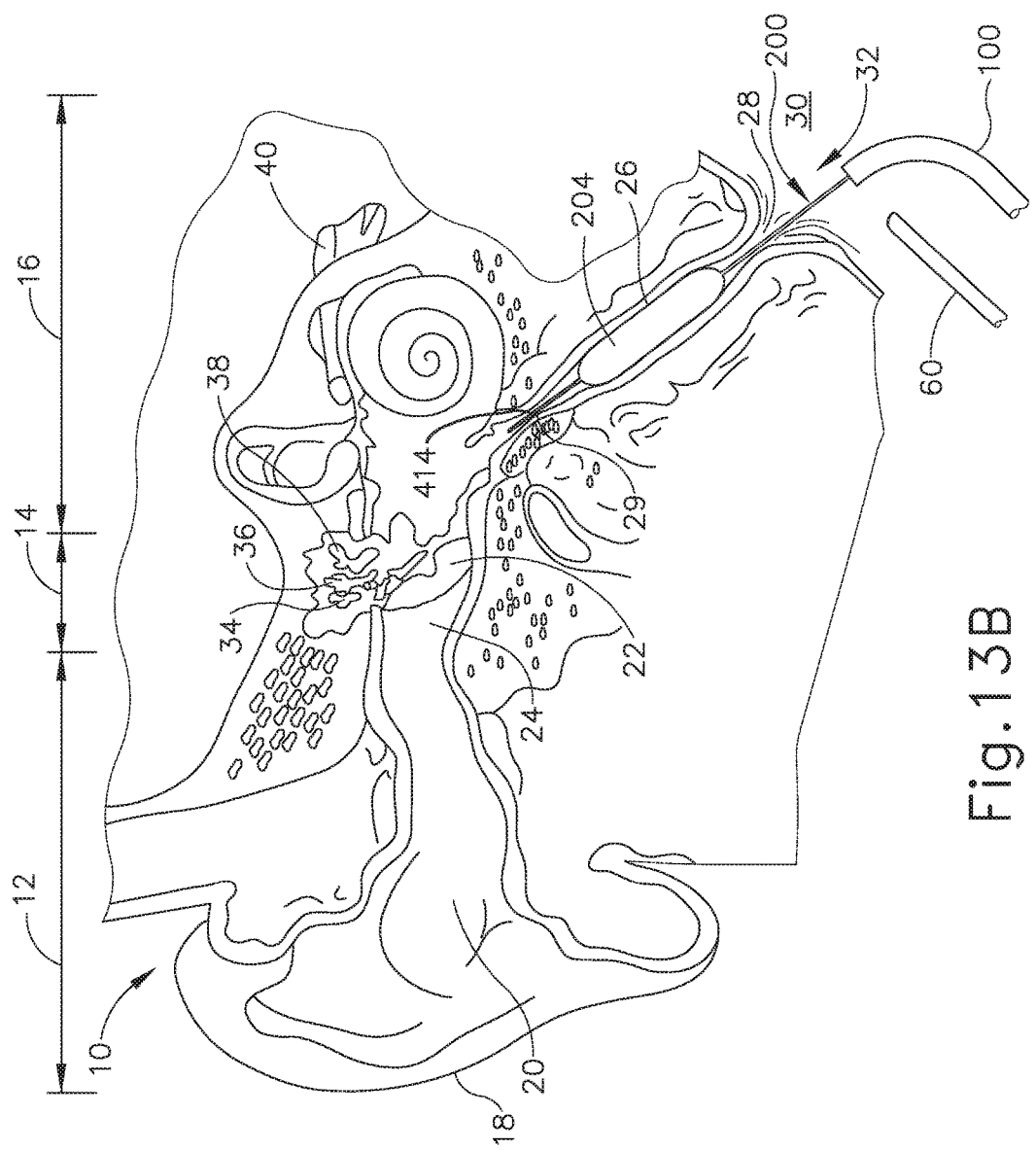
FIG. 13B depicts a cross-sectional view of the guide catheter and endoscope of FIG. 13A, with a balloon catheter and an instrument for treating an isthmus being positioned in relation to the Eustachian tube and isthmus, with a balloon of the balloon catheter being expanded to dilate the Eustachian tube.

FIGS. 13A-E show an exemplary method of using instrument (400) to clean the isthmus (29), depicting partially schematic versions of guide catheter (100), balloon catheter (200), and instrument (400). FIGS. 13A-B show a similar method being performed to dilate the ET (26) as described above with respect to FIGS. 10A-B, with the only difference being that in this instance, the isthmus (29) is clogged or otherwise obstructed, and instrument (400) has been loaded into balloon catheter (200), according to one of the manners described herein. FIG. 13A shows guide catheter (100) being positioned at or near an opening of the ET (26) over guidewire (500), under the visual guidance of endoscope (60). FIG. 13B shows a similar step as described with respect to FIG. 10B, however, instrument (400) is shown to have been loaded into balloon catheter (200), with distal shaft (410) and expandable element (414) protruding distally from the distal end (218) of balloon catheter (200), in a manner described above, such that balloon (404) is positioned to dilate the ET (26) and expandable element (414) is adjacent to or coincident with the isthmus (29), such that the clog or obstruction in the isthmus (29) may be cleared.

In some versions, the light on tip (412) of instrument (400) may be used to assist in the confirmation whether the isthmus (29) or ET (26) is in fact clogged or otherwise obstructed. For example, the operator may view the tympanic membrane (22) via the ear canal (20) using any suitable form of visualization, while tip (412) is illuminated in or near the isthmus (29). If the light from tip (412) illuminates the tympanic membrane (22), this may indicate that the isthmus (29) is sufficiently clear such that instrument (400) does not need to be actuated in order to clear the isthmus (29). However, if the light from tip (412) does not illuminate the tympanic membrane (22), the lack of illumination may be an indication that the isthmus (29) is clogged or otherwise constricted.

Figure 13C:
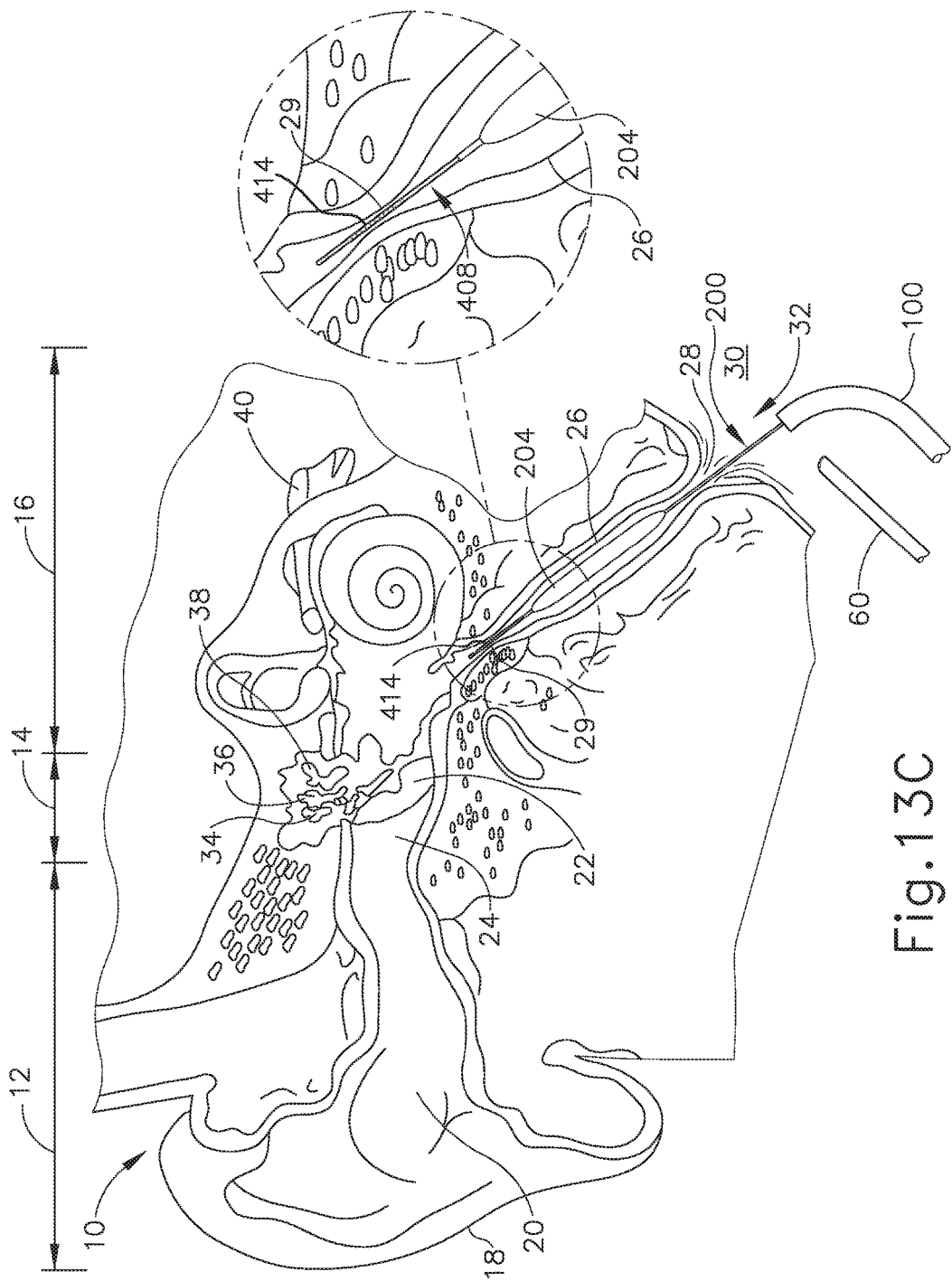
FIG. 13C depicts a cross-sectional view of the guide catheter, endoscope, and instrument of FIG. 13B, showing the instrument being positioned in relation to the isthmus and an expandable element of the instrument in a contracted configuration.
Figure 13D:
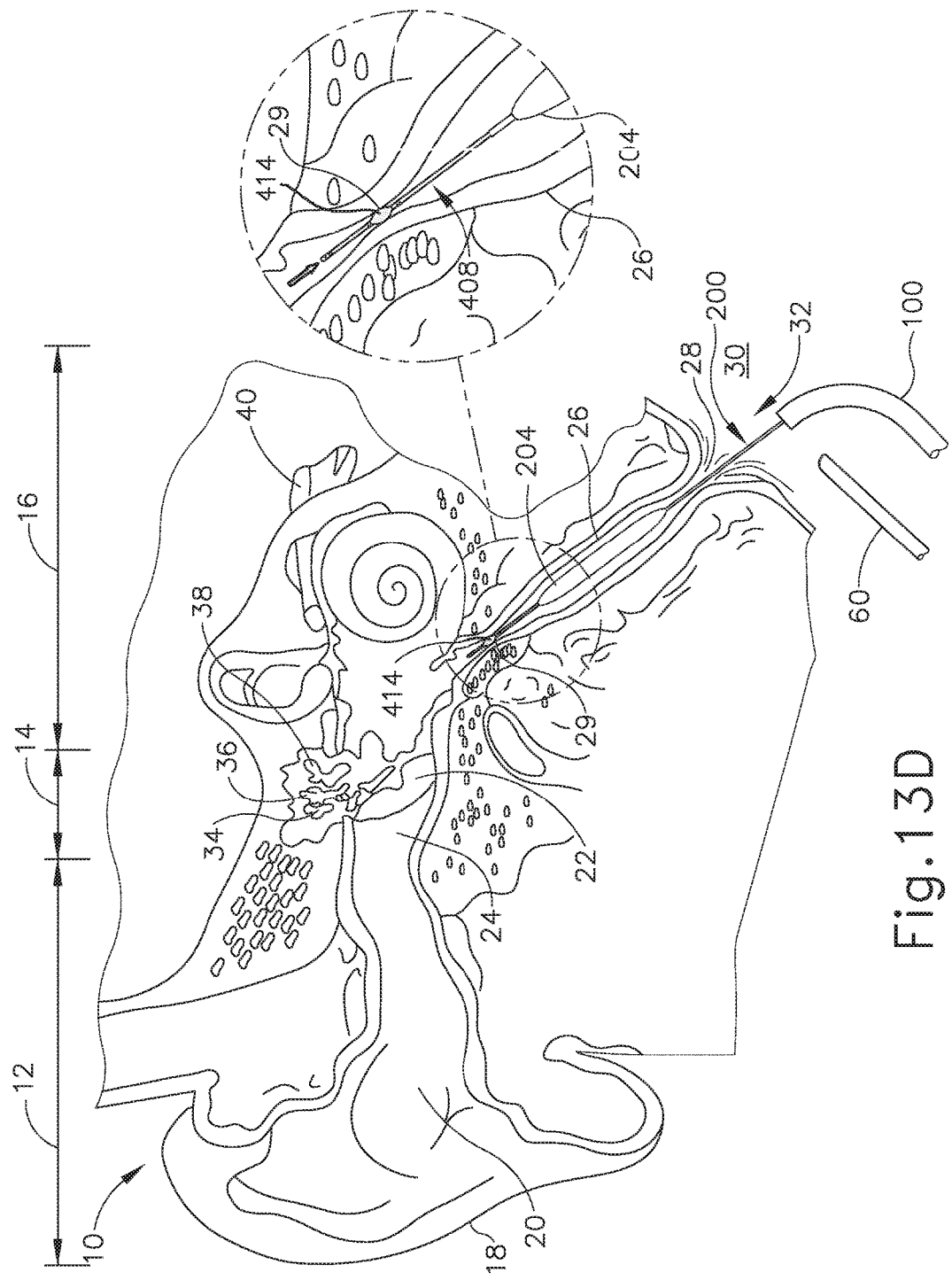
FIG. 13D depicts a cross-sectional view of the guide catheter, endoscope, and instrument of FIG. 13B, showing an expandable element of the instrument in an expanded configuration.
Figure 13E:
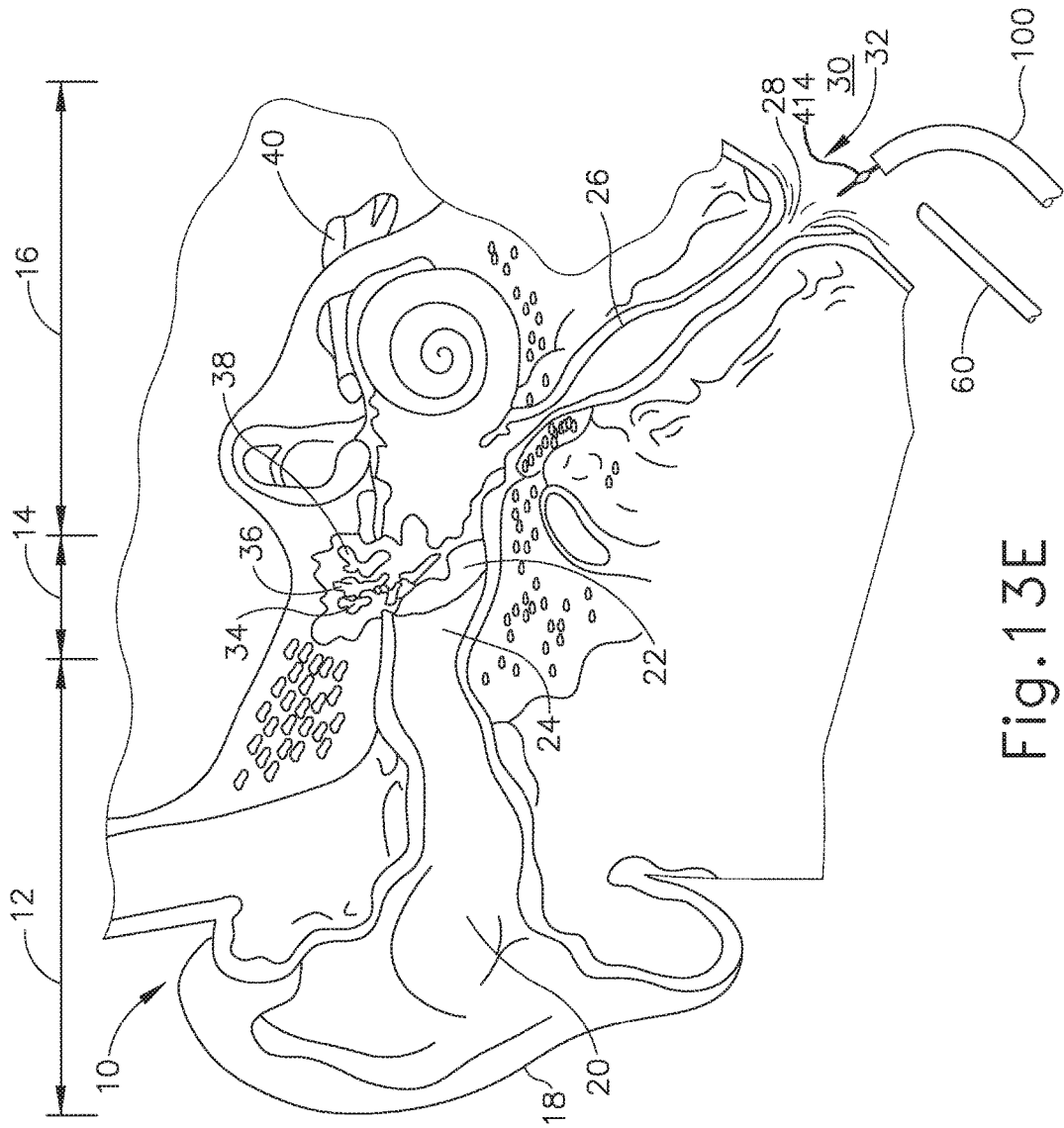
FIG. 13E depicts a cross-sectional view of the guide catheter, endoscope, and instrument of FIG. 13B, showing the expandable element of the instrument in an expanded configuration and showing the instrument in a retracted position relative to the isthmus and the Eustachian tube.

As shown in FIG. 13B, balloon (202) is expanded to dilate the ET (26) in the same or similar manner described with respect to FIG. 10B. In alternative examples, rather than instrument (400) being loaded into balloon catheter (200) before balloon catheter traverses guide catheter (100), such that instrument (400) and balloon catheter (200) travel as a unit, instrument (400) may be loaded into balloon catheter (200) after balloon catheter (200) has reached the position shown in FIG. 13B, for example, before or after dilation occurs. Referring to FIG. 13C, balloon (204) is deflated after dilating the ET (26) one or more times. The expandable element (414) is then expanded via the actuator (420) being directed in the proximal direction, or in one of the other manners described above. Then, as shown in FIG. 13D-E, balloon catheter (200) and instrument (400) are retracted, as a unit, so that expandable element (414) drags against the walls of the isthmus (29), and captures any material or debris clogging or obstructing the isthmus (29). In some examples, it may be undesirable for the expandable element (414) to drag against the walls of the ET (26) after dragging against the walls of the isthmus (29). Therefore, the expandable element (414) in the expanded may be sized and configured to be smaller than a cross-sectional dimension of the ET (26) (before or after dilation of the ET (26)). Additionally or alternatively, the expandable element (414) may be transitioned to the contracted configuration after the expandable element (414) has been dragged against the walls of the isthmus (29), to reduce the likelihood that the expandable element (414) drag against the walls of the ET (26). In other examples, however, where it may be desirable for expandable element (414) to drag against the walls of the ET (26), expandable element (414) may be sized and configured to drag against both the walls of the isthmus (29) and the ET (26).

In the present example, balloon (204) is deflated before expandable element (414) is expanded. In some other versions, balloon (204) remains inflated as expandable element is expanded. In some situations, inflated balloon (204) may provide additional friction and thereby provide a mechanical ground or anchor, reducing a risk that expandable element (414) may inadvertently translate longitudinally within the isthmus (29) when expandable element (414) is transitioned to the expanded state.

In the present example, the braided wire mesh configuration of expandable element (414) is configured to scrape against the walls of the isthmus (29) and/or the ET (26) with a sufficient amount of friction to remove debris but not so much friction such that the isthmus (29) and/or ET (26) will be damaged. Moreover, due to the fragile structures adjacent to the isthmus (29), the expandable element (414) is configured to expand and contract as it traverses and contacts walls of the isthmus (29) and ET (26); and is also configured such that it has little to no dilating effect on the tissue of the isthmus (29) and ET (26). In that regard, in some examples, the expandable element (414), in the expanded configuration, may be configured to be compressed down to a size approximately equal to the cross-sectional dimension of the smallest opening of the isthmus (26), to minimize or eliminate the dilating effect of the expandable element (414), such that no permanent dilation of the isthmus (29) takes place, but to still maintain contact with the walls of the isthmus (29) for effective cleaning of the isthmus (29). Moreover, in some examples, the cross-sectional dimension of the expandable element (414) in the unexpanded configuration may be smaller than the cross-sectional dimension of the smallest opening of the isthmus (29).

As shown in FIG. 13E, the debris removed from isthmus (29) by expandable element (414) is retracted into guide catheter (100) as balloon catheter (200); and instrument (400), after being transitioned to its unexpanded configuration, is retracted along with balloon catheter (200) relative to the guide catheter (100). In other examples, the debris may be flushed or otherwise removed from the nasopharynx or other portions of the oro-nasal cavity once removed from the isthmus (29) and/or ET (26). The balloon catheter (200) may be re-inserted for subsequent dilations of the ET (26), or for other therapies, such as the therapies described herein. To confirm whether the isthmus (29) has been cleared sufficiently, the operator may again utilize the light source of on tip (412) of instrument (400). For example, the operator may view the tympanic membrane (22) via the ear canal (20) using any suitable form of visualization, while tip (412) is illuminated in or near the isthmus (29). If the light from tip (412) illuminates the tympanic membrane (22), this may indicate that the isthmus (29) is sufficiently clear. However, if the light from tip (412) does not illuminate the tympanic membrane (22) or if the intensity of the light passing through to the tympanic membrane (22) is relatively low, this may indicate that the isthmus (29) is not sufficiently clear. In such instances, the operator may attempt to clear the isthmus (29) again using one of the techniques described herein.

In addition or as an alternative to instrument (400), other exemplary instruments may be used in order to clean or otherwise clear the isthmus (29). Such instruments, as shown in FIGS. 14-24 may be used in combination with some, all, or one of guide catheter (100), balloon catheter (200), and/or endoscope (60), where applicable. For example, some of the instruments shown in FIGS. 14-24, where applicable, may be used in the manners as shown in FIGS. 10A-B and FIGS. 13A-E (e.g., in conjunction with dilation using balloon catheter (200), travel as a unit with balloon catheter, in conjunction with guide catheter (100, 300), etc). However, some of the instruments of FIGS. 14-24 may or may not be used in conjunction with balloon catheter (200) and/or guide catheter (100). For example, some of the instruments may be inserted into the ET (26) via the guide catheter 100), without the balloon catheter (200) being used at all; or if balloon catheter (200) has been used for dilation, the instruments may be inserted through the guide catheter (100) after balloon catheter (200) has been removed. Moreover, as will be seen below, some of the instruments themselves are capable of dilating the ET (26). Moreover, any of the therapies described herein, including but not limited to balloon dilation using balloon catheter (200), for example, may be used in conjunction with the instruments shown in FIGS. 14-24.

Figure 14:
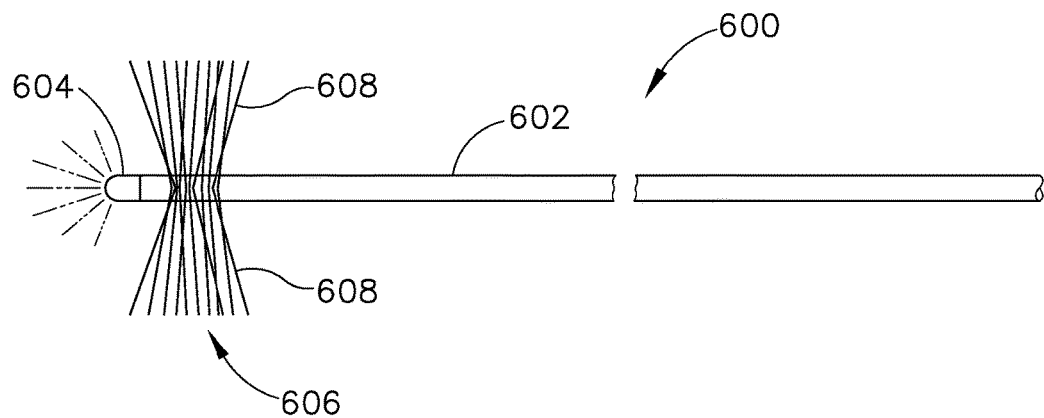
FIG. 14 depicts a side elevational view of another exemplary instrument that may be used to treat a Eustachian tube isthmus via the balloon catheter of FIG. 5A.

One exemplary alternative instrument (600) for cleaning the isthmus, as shown in FIG. 14, includes a shaft (602) and an atraumatic, rounded tip (604). Shaft may be bendable to traverse anatomical structures (e.g., oro-nasal cavity) and other devices (e.g., guide catheter (100) and balloon catheter (200)). Similar to tip (412), tip (604) may include an illuminating feature so that the clogged or obstructed state of the ET (26) may be observed via the external ear (12) as described above. Instrument (600) further includes a brush feature (606) defined by a plurality of bristles (608).

In an exemplary use, instrument (600) may be backloaded or frontloaded into balloon catheter (200), for example, such that the brush feature (606) and balloon catheter (200) may be directed into the ET (26) as a unit, in a similar manner as instrument (400) and balloon catheter (200) described above. Balloon catheter (200) and instrument (600) may or may not be advanced as a unit within the ET (26) until the distal end of balloon catheter (200) positioned in the ET (26). Instrument (600) is then advanced out of distal end (218) of balloon catheter (200) into the isthmus (29), thereby exposing bristles (608). Alternatively, balloon catheter (200) may be retracted relative to instrument (600) in order to expose brush feature (606). In some instances, instrument (600) may include a retractable sheath that contains the bristles (608) when the sheath is in a distal position. In some such versions, the sheath may be in the distal position as the distal end of instrument (600) is advanced into the isthmus (29). Once the instrument (600) has reached position adjacent to or coincident with the isthmus (29), the sheath can be retracted to expose the bristles (608).

Once brush feature (606) is exposed, instrument (600) and balloon catheter (200) (if still present) may be retracted in order that bristles (608) of brush feature (606) sweep or scrape against the walls of the isthmus (29) and/or ET (26) to clean and clear any debris therein. Instrument (600) may, additionally or alternatively, be rotated or reciprocated relative to the isthmus (29) in order to clear the isthmus (29). Once brush feature (606) is utilized to clear debris in the isthmus (29), instrument (600) may be removed in a similar manner as described with respect to instrument (400). For example, instrument (600) may be removed as a unit with the balloon catheter (200) (if used), or may be removed before the balloon catheter (200) (if used). In examples including the retractable sheath, the sheath can stay in the proximal position for the remainder of the procedure once it is retracted. Alternatively, the sheath can be advanced to re-cover bristles (608) before instrument (600) is retracted through balloon catheter (200) or through guide catheter (100).

Figure 15B:
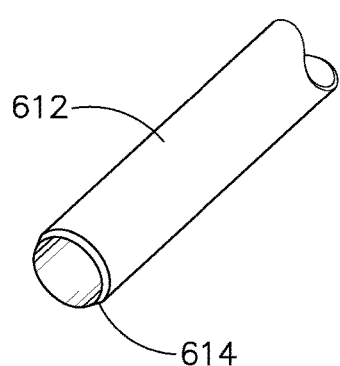
FIG. 15B depicts a detailed perspective view of a distal end of the instrument of FIG. 15A.
Figure 15A:
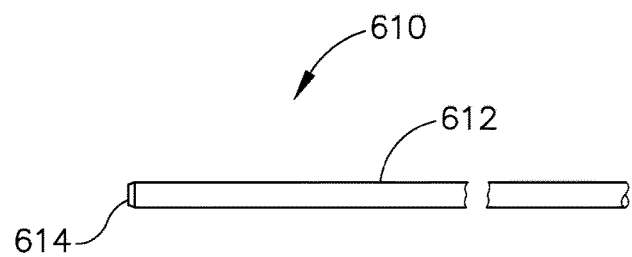
FIG. 15A depicts a side elevational view of another exemplary instrument that may be used to treat a Eustachian tube isthmus via the balloon catheter of FIG. 5A.

FIGS. 15A and 15B show another exemplary instrument (610) that may be used to clean the isthmus (29). Instrument (610) of this example includes a shaft (612) and a distal cutting feature (614). In the present example, at least the distal end of shaft (612) is hollow; and the distal cutting feature (614) comprises a circular blade formed by the distal edge of shaft (612). Thus, the distal end of the shaft (612) is formed as a coring instrument. Shaft (612) may be bendable to traverse anatomical structures (e.g., oro-nasal cavity) and other devices (e.g., guide catheter (100) and balloon catheter (200)). In one exemplary use, instrument (610) may be backloaded or frontloaded into balloon catheter (200), for example, such that the distal cutting feature (614) is adjacent to but still within distal end (218) of balloon catheter (200). Instrument (610) and balloon catheter (200) may or may not be directed into the ET (26) as a unit, in a similar manner as instrument (400) and balloon catheter (200) described above. Once instrument (610) is within the ET (26), the instrument (610) may then be moved relative to balloon catheter (200) (via either advancement of instrument (610) or retraction of balloon catheter (200)) and distal cutting feature (614) may be directed toward the clog/debris to cut the clog/debris. In one example, distal cutting feature (614) is configured to retain the clog/debris material therein once it cuts the clog/debris material, similar to a conventional cylindraceous coring instrument. After removing the clog/debris, instrument (614) may then be refracted from the isthmus (29) as described above.

Figure 16:
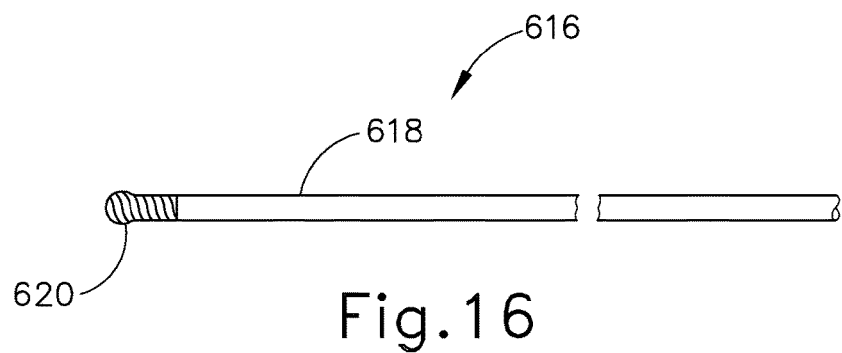
FIG. 16 depicts a side elevational view of another exemplary instrument that may be used to treat a Eustachian tube isthmus via the balloon catheter of FIG. 5A.

FIG. 16 shows another exemplary alternative instrument (616) that may be used to clean the isthmus (29). Instrument (616) includes a shaft (618) with a burr feature (620) at a distal end thereof. Shaft (618) may be bendable to traverse anatomical structures (e.g., oro-nasal cavity) and other devices (e.g., guide catheter (100) and balloon catheter (200)). Burr feature (620) may include various shapes and pitches that are different than that seen in FIG. 16. In one exemplary use, instrument (616) may be backloaded or frontloaded into balloon catheter (200), for example, such that the burr feature (620) is adjacent to but still within distal end (218) of balloon catheter (200). Instrument (616) and balloon catheter (200) may or may not be directed into the ET (26) as a unit, in a similar manner as instrument (400) and balloon catheter (200) described above. Once instrument (616) is within the ET (26), the instrument (610) may then be moved relative to balloon catheter (200) (via either advancement of instrument (616) or retraction of balloon catheter (200)) and burr feature (620) may be directed toward the clog/debris to disrupt and remove the clog/debris. Instrument (616) may be reciprocated and/or rotated relative to the ET (26) and isthmus (29) in order to take advantage of the grooves of burr feature (620) in dislodging or cutting the clog/debris. Instrument (616) may then be retracted from the isthmus (29) as described above.

Figure 17:
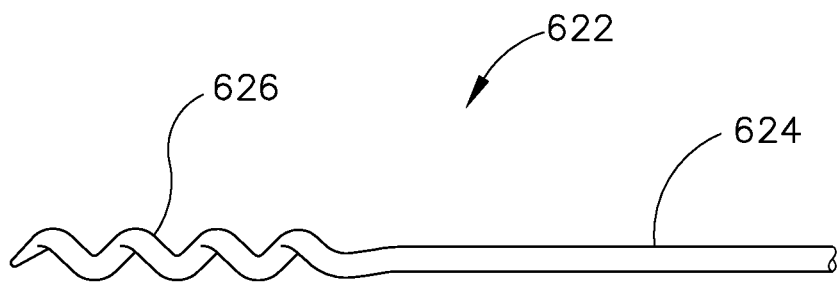
FIG. 17 depicts a side elevational view of another exemplary instrument that may be used to treat a Eustachian tube isthmus via the balloon catheter of FIG. 5A.

FIG. 17 shows another exemplary alternative instrument (622) that may be used to clean the isthmus (29). Instrument (622) includes a shaft (624) with a corkscrew feature (626) at a distal end thereof. Shaft (624) may be bendable to traverse anatomical structures (e.g., oro-nasal cavity) and other devices (e.g., guide catheter (100) and balloon catheter (200)). Corkscrew feature (626) may include various shapes and pitches that are different than the shape and pitch seen in FIG. 16. By way of example only, corkscrew feature (626) may alternatively be configured like a helical auger blade. In one exemplary use, instrument (622) may be backloaded or frontloaded into balloon catheter (200), for example, such that the corkscrew (626) is adjacent to but still within distal end (218) of balloon catheter (200). Instrument (622) and balloon catheter (200) may or may not be directed into the ET (26) as a unit, in a similar manner as instrument (400) and balloon catheter (200) described above. Once instrument (622) is within the ET (26), the instrument (610) may then be moved relative to balloon catheter (200) (via either advancement of device (62) or retraction of balloon catheter (200)) and corkscrew feature (620) may be directed toward the clog/debris to drive through and remove the clog/debris. Instrument (622) may be reciprocated and rotated relative to the ET (26) and isthmus (29) in order to take advantage of the corkscrew feature (626) in dislodging or cutting the clog/debris. Instrument (622) may then be retracted from the isthmus (29) as described above.

Figure 18:
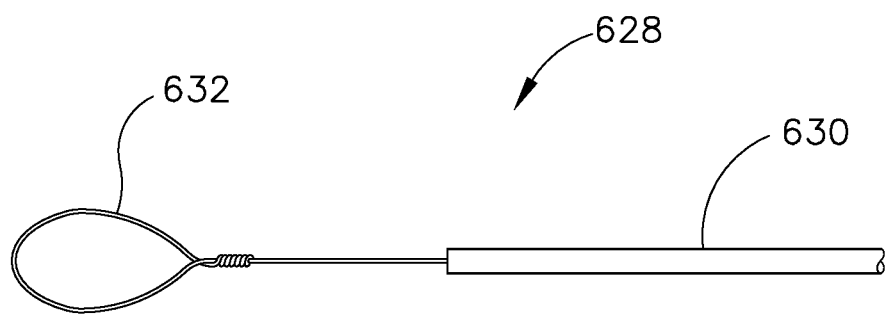
FIG. 18 depicts a side elevational view of another exemplary instrument that may be used to treat a Eustachian tube isthmus via the balloon catheter of FIG. 5A.

FIG. 18 shows another exemplary alternative instrument (628) that may be used to clean the isthmus (29). Instrument (628) includes a shaft (630) with wire snare feature (632) at a distal end thereof. Shaft (630) may be bendable to traverse anatomical structures (e.g., oro-nasal cavity) and other devices (e.g., guide catheter (100) and balloon catheter (200)). Snare feature (632) is advanceable and retractable relative to shaft (630) via a feature on proximal end (not shown) of shaft (630). Snare feature (632) and may include various shapes and features that are different than those shown in FIG. 18. In one exemplary use, instrument (628) may be backloaded or frontloaded into balloon catheter (200), for example, with snare feature (632) retracted into the shaft (630), and such that distal end of shaft (630) is still within distal end of balloon catheter (200). Instrument (628) and balloon catheter (200) may or may not be directed into the ET (26) as a unit, in a similar manner as instrument (400) and balloon catheter (200) described above. Once instrument (628) is within the ET (26), the instrument (628) may then be moved relative to balloon catheter (200) (via either advancement of instrument (628) or retraction of balloon catheter (200)). Snare feature (632) may then be advanced to ensnare the clog/debris. Snare feature (632) may be configured to dislodge, grab hold of, and retract clog/debris into shaft (630). After removing the clog/debris, instrument (628) may then be retracted from the isthmus (29) as described above.

Figure 19:
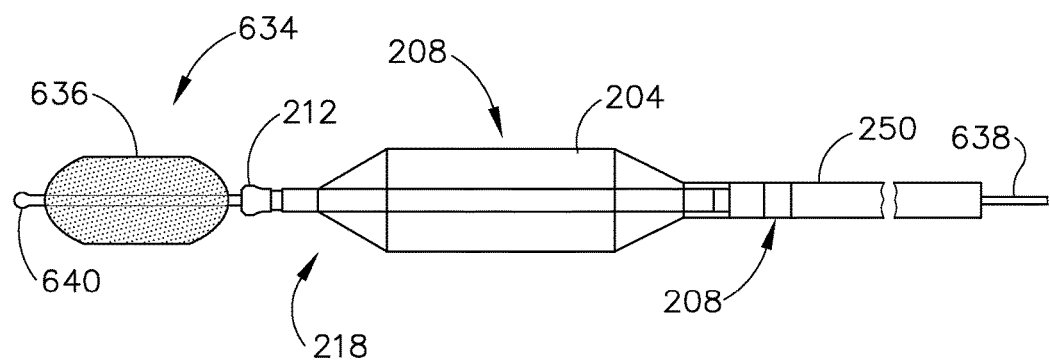
FIG. 19 depicts a side elevational view of another exemplary instrument that may be used to treat a Eustachian tube isthmus via the balloon catheter of FIG. 5A, with an expandable element of the instrument in an expanded configuration.

FIG. 19 shows another exemplary alternative instrument (634) that may be used to clean the isthmus (29). Instrument (634) is similar to instrument (400) in that it includes expandable element (636), which as shown is an expandable balloon with an abrading outer surface, rather than a mesh structure. Instrument (634) includes a shaft (638) having expandable balloon (636) on a distal end thereof that is, in one example, inflatable at a lower pressure than the inflating pressure of balloon (204) of balloon catheter (200), due to the sensitive nature of structures adjacent to the isthmus. Moreover, expandable element (636) expands to a smaller outer cross-sectional dimension than the expanded outer cross-sectional dimension of balloon (204) so that it may extend within the isthmus (29), and to reduce the likelihood of damage to the isthmus (29) and surrounding structures upon expanding expandable element (636). Instrument (634) includes an atraumatic tip (640) that is configured to prevent damage to the ET (26), isthmus (29), and surrounding structures. Instrument (634) may be introduced into the ET (26) in the same or similar manner as instrument (400), such that expandable member (636) extends past the distal end of balloon catheter (200).

In one example, after balloon (204) of balloon catheter (200) is deflated, instrument (634) is advanced further within the ET (26) (with or without balloon catheter (200)) such that expandable element (636) is positioned past the clog or obstruction in the isthmus (29). Expandable element (636) is then expanded, such as in a similar manner as the expansion of balloon (204) (but at a lower pressure), or in another manner understood by persons skilled in the art according to the teachings herein. Then, in one example, balloon catheter (200) and instrument (634) are retracted, as a unit, so that abrading surface of expandable element (636) drags against the walls of the isthmus (29) and captures any material or debris clogging or obstructing the isthmus (29). In some examples, it may be undesirable for the expandable element (636) to drag against the walls of the ET (26) after dragging against the walls of the isthmus (29). Therefore, the expandable element (636) in the expanded may be sized and configured to be smaller than a cross-sectional dimension of the ET (26) (before or after dilation). Additionally or alternatively, the expandable element (636) may be transitioned to the contracted configuration after the expandable element (636) has been dragged against the walls of the isthmus (29), to reduce the likelihood that the expandable element (636) drag against the walls of the ET (26). In other examples, however, where it may be desirable for expandable element (636) to drag against the walls of the ET (26), expandable element (636) may be sized and configured to drag against both the walls of the isthmus (29) and the ET (26).

In the present example, the abraded configuration of the expandable element (636) is configured to scrape against the walls of the isthmus (29) and/or ET (26) with a sufficient amount of friction to remove debris but not so much friction such that the isthmus (29) and/or ET (29) will be damaged. Moreover, due to the fragile structures adjacent to the isthmus (29), the expandable element (636) may be configured to expand and contract as it traverses and contacts walls of the isthmus (29) and ET (26), and is also configured such that it has little to no dilating effect on the tissue of the isthmus (29) and ET (26), such that no permanent dilation of the isthmus (29) occurs. In that regard, in some examples, the expandable element (636), in the expanded configuration, may be configured to be compressed down to a size approximately equal to the cross-sectional dimension of the smallest opening of the isthmus (29), to minimize or eliminate the dilating effect of the expandable element (636), but to still maintain contact with the walls of the isthmus for effective cleaning of the isthmus (29). Moreover, in some examples, the cross-sectional dimension of the expandable element (636) in the unexpanded configuration may be smaller than the cross-sectional dimension of the smallest opening of the isthmus (29).

After expandable element (636) is used to clean the isthmus (29), it may be retracted back into balloon catheter (200). Then, as a unit, instrument (634) and balloon catheter (200) may be withdrawn through guide catheter (100).

Figure 20:
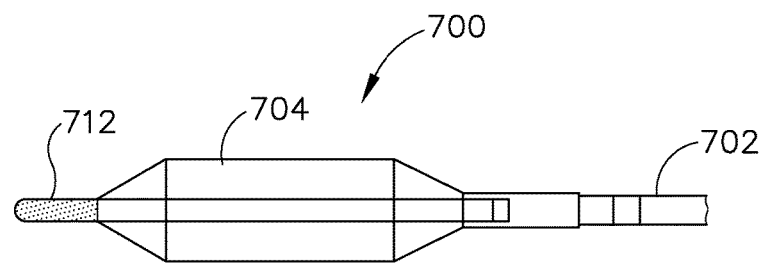
FIG. 20 depicts a side elevational view of a distal portion of an exemplary alternative balloon dilation catheter that may be used with the guide catheter of FIG. 3A.

FIG. 20 shows another exemplary alternative instrument (700) that may be used to clean the isthmus (29). Instrument (700) of this example is a modified version of balloon dilation catheter (200). As shown, instrument (700) includes a shaft (702) and balloon (704) that are identical to shaft (202) and balloon (204), respectively, as described above. Instrument (700) also includes an atraumatic tip (712) that is sized and configured to pass through the isthmus (29). Tip (712) includes an abraded surface treatment or coating. In use, after balloon (704) is used to dilate the ET (26), balloon (704) is deflated and tip (712) is advanced toward the clog/debris of the isthmus (29) in order to dislodge it. In some versions, instrument (700) of FIG. 20 may be used in combination with any of the instruments shown in FIGS. 14-19. It should also be understood that instrument (700) may be removed from the isthmus (29) and the ET (26) as described above.

Figure 21:
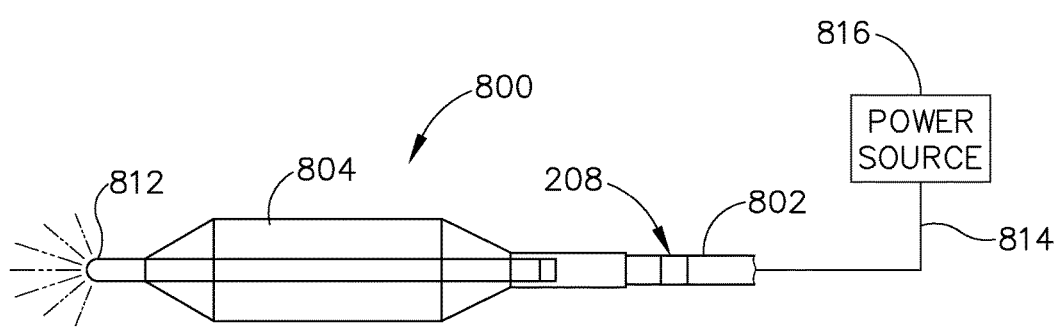
FIG. 21 depicts a side elevational view of a distal portion of another exemplary balloon dilation catheter that may be used with the guide catheter of FIG. 3A.

FIG. 21 shows another exemplary alternative instrument (800) that may be used to clean the isthmus (29). Instrument (800) of this example is a modified version of balloon dilation catheter (200). As shown, instrument (800) includes a shaft (802) and balloon (804) that are identical to shaft (802) and balloon (804), respectively, as described above. Instrument (800) also includes an atraumatic tip (812) that is sized and configured to pass through the isthmus (29). Moreover, tip (812) is active such that tip (812) is capable of delivering energy to the isthmus (29). By way of example, tip (812) may be configured to deliver ultrasonic vibrational energy, RF electrical energy, and/or any other suitable form of energy. In that regard, instrument further includes a line (814) configured to connect tip (812) to a power source (816). In some versions, tip (812) includes one or more RF energy electrodes, the power source (816) comprises a source of RF electrosurgical energy, and line (814) connecting power source (816) with tip (812) comprises one or more wires. In some other versions, power source (816) comprises an ultrasonic transducer, and line (814) connecting power source (816) comprises an ultrasonic waveguide. Alternatively, tip (812) itself may include the ultrasonic transducer, such that line (814) between power source (816) and tip (812) is one or more wires configured to deliver electrical power.

Regardless of whether the energy is RF, ultrasonic, and/or some other form of energy, such energy delivered from power source (816) through line (814) and to tip (812) may be configured to break through a clog or debris in the isthmus (29). Various suitable features that may be incorporated into instrument (800) in order to provide delivery of ultrasonic vibrational energy, RF electrical energy, and/or other suitable forms of energy through tip (812) will be apparent to those of ordinary skill in the art in view of the teachings herein. In use, after balloon (804) is used to dilate the ET (26), balloon (804) is deflated and tip (812) is advanced toward clog/debris of isthmus (29) in order to dislodge the clog/debris, using contact of tip (812), as well as the energy delivered by tip (812). After removing the clog/debris, instrument (800) may then be retracted from the isthmus (29) and the ET (26) as described above.

FIGS. 22 and 22A show another exemplary instrument (900) that may be used to clean the isthmus (29). Instrument of this example includes an illuminated distal portion (902) terminating into a tip (904), a power source (910) having an activation mechanism (905), and an elongated portion (906) connecting power source (910) with illuminated distal portion (902). Activation mechanism (905) is configured to activate or deactivate power source (910). Illuminated distal portion (902) is configured to emit light. In some versions, the light from illuminated distal porting (902) of instrument (900) may be used to assist in the confirmation whether the isthmus (29) or ET (26) is in fact clogged or otherwise obstructed. For example, the operator may view the tympanic membrane (22) via the ear canal (20) using any suitable form of visualization, while illuminated distal portion (902) is illuminated in or near the isthmus (29). If the light from illuminated distal portion (902) illuminates the tympanic membrane (22), this may indicate that the isthmus (29) is sufficiently clear such that instrument (900) does not need to be actuated in order to clear the isthmus (29). However, if the light from illuminated distal portion (902) does not illuminate the tympanic membrane (22), the lack of illumination may be an indication that the isthmus (29) is clogged or otherwise constricted.

In some versions, illuminated distal portion (902) extends distally from distal end (218) such that tip (904) of distal portion (902) is approximately 1 cm from distal tip (212) of catheter (200). Alternatively, distal portion (902) may extend to any other suitable length. In versions where distal portion (902) is slidable relative to catheter (200), a hard stop may be included to prevent distal portion (902) from being advanced distally beyond a point where tip (904) of distal portion (902) is approximately 1 cm (or some other predetermined distance) from distal tip (212) of catheter (200). By way of example only, illuminated distal portion (902) may comprise an LED embedded in tip (904). In some such versions, wires or other electrical conduits may extend along elongated portion (906) to provide electrical power from power source (910) to the LED. As another merely illustrative example, the power source (910) may generate light, and the generated light may travel through one or more optical fibers that extend through elongated portion (906) toward illuminated distal portion (902). Other suitable forms that the light source may take will be apparent to those of ordinary skill in the art in view of the teachings herein.

It should be understood that at least a portion of illuminated distal portion (902) may be sized and configured to be received within lumen (234) of balloon catheter (200). In one exemplary use, instrument (900) may be backloaded or frontloaded into balloon catheter (200), similar to the methods referenced above. Instrument (900) and balloon catheter (200) may or may not be directed into the ET (26) as a unit, in a similar manner as instrument (400) and balloon catheter (200) described above. By way of example only, some versions of instrument (900) may comprise an illuminated guidewire that is slidably disposed in balloon catheter (200), with the distal end of the illuminated guidewire serving as illuminated distal portion (902). The illuminated guidewire may be provided in accordance with the teachings of U.S. Pub. No. 2012/0078118, entitled "Sinus Illumination Lightwire Device," published Mar. 29, 2012, issued as U.S. Pat. No. 9,155,492 on Oct. 13, 2015, the disclosure of which is incorporated by reference herein. An example of such an illuminating guidewire is the Relieva Luma Sentry™ Sinus Illumination System by Acclarent, Inc. of Menlo Park, Calif. Other suitable forms that an illuminating guidewire may take will be apparent to those of ordinary skill in the art in view of the teachings herein.

As yet another merely illustrative alternative, instrument (900) may constitute a modified version of balloon dilation catheter (200). As such, distal portion (902) may unitarily extend distally from distal end (218) of balloon catheter (200). Regardless of whether illuminated distal portion (902) is integral with dilation catheter (200) or a separate component that is slidable relative to dilation catheter (200), illuminated distal portion (902) may be bendable to traverse anatomical structures (e.g., oro-nasal cavity) and other devices (e.g., guide catheter (100) and balloon catheter (200). In the present example, tip (904) includes an atraumatic, rounded end and is configured and sized to pass through isthmus (29). Tip (904) is further configured to prevent damage to structures within the middle ear (14) and other portions of the oro-nasal cavity as instrument (900) traverses the anatomy.

In use, after balloon (204) is used to dilate the ET (26), balloon (204) is deflated and tip (904) is advanced toward the clog/debris of the isthmus (29) in order to dislodge the clog/debris of the isthmus (29) and/or otherwise dilate the isthmus (29). In some versions, tip (904) is advanced independently of balloon catheter (200). In other versions, tip (904) travels unitarily with balloon catheter (200). In some versions, instrument (900) of FIG. 22 may be used in combination with any of the instruments shown in FIGS. 14-21. It should also be understood that instrument (900) may be removed from the isthmus (29) and the ET (26) as described above.

Figure 23:
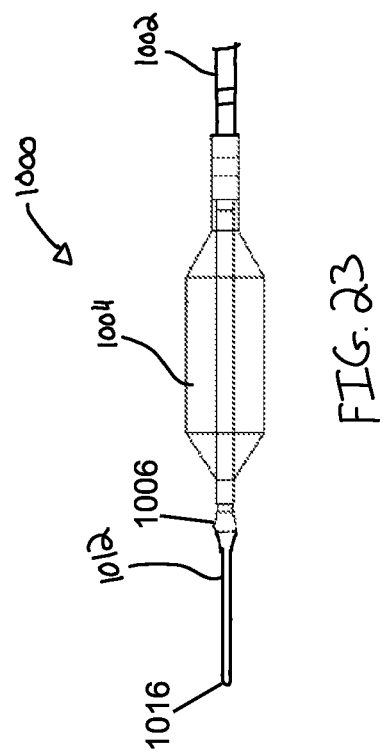
FIG. 23 depicts a side elevational view of a distal portion of an exemplary alternative balloon dilation catheter that may be used with the guide catheter of FIG. 3A.

FIG. 23 shows another exemplary alternative instrument (1000) that may be used to clean the isthmus (29). Instrument (1000) of this example is a modified version of balloon dilation catheter (200). As shown, instrument (1000) includes a shaft (1002) and balloon (1004) that are identical to shaft (202) and balloon (204), respectively, as described above. Instrument (1000) also includes an atraumatic, necked-down tip (1012) that is sized and configured to pass through the isthmus (29). By way of example only, necked-down tip (1012) may be formed by a solid polymer, without a lumen extending therethrough. Alternatively, tip (1012) may include a lumen extending therethrough. In some versions, tip (1012) extends distally from the distal tip (1006) of shaft (1002) such that the distal end (1016) of tip (1012) is approximately 1 cm from distal tip (1006) of shaft (1002). In use, after balloon (1004) is used to dilate the ET (26), balloon (1004) is deflated and tip (1012) is advanced toward the clog/debris of the isthmus (29) in order to dislodge the clog/debris of the isthmus (29) and/or otherwise dilate the isthmus (29). In some versions, instrument (1000) of FIG. 23 may be used in combination with any of the instruments shown in FIGS. 14-22A. It should also be understood that instrument (700) may be removed from the isthmus (29) and the ET (26) as described above.

Figure 24:
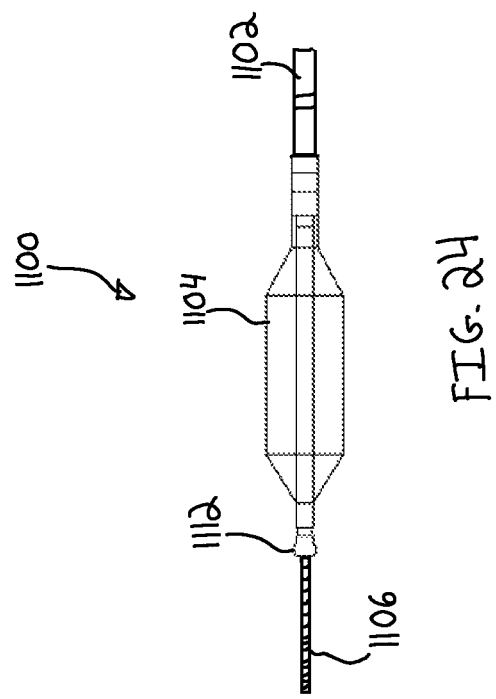
FIG. 24 depicts a side elevational view of a distal portion of another exemplary alternative balloon dilation catheter that may be used with the guide catheter of FIG. 3A.

FIG. 24 shows another exemplary alternative instrument (1100) that may be used to clean the isthmus (29). Instrument (1100) of this example is a modified version of balloon dilation catheter (200). As shown, instrument (1100) includes a shaft (1102), a balloon (1104), and an atraumatic tip (1112) that are identical to shaft (202), balloon (204), and atraumatic tip (212) respectively, as described above. Instrument (700) also includes a guidewire (1106) extending distally from atraumatic tip (1112) that is sized and configured to pass through the isthmus (29). Guidewire (1106) may comprise coiled stainless steel, a polymer, and/or any other suitable material(s) as will be apparent to those of ordinary skill in the art in view of the teachings herein. Guidewire (1106) may also include a hydrophilic coating. By way of example only, guidewire (1106) may extend to a length of approximately 1 cm from atraumatic tip (1112).

In some versions, guidewire (1106) is fixedly secured to shaft (1102) such that guidewire (1106) is advanced into the isthmus (29) by advancing shaft (1102) in the ET (26). When guidewire (1106) is advanced into the isthmus (29), guidewire (1106) may dislodge any clog/debris of the isthmus (29) and/or otherwise dilate the isthmus (29). In some other versions, guidewire (1106) is slid distally relative to shaft (1102) to enable advancement of guidewire (1106) into the isthmus (29). In such versions, guidewire (1106) may include a hard stop that prevents guidewire (1106) from being advanced beyond a point where guidewire (1106) extends approximately 1 cm from atraumatic tip (1112). It should also be understood that, in some versions, instruments such as the instruments shown in FIGS. 14-19 and FIGS. 22 and 22A may slide over guidewire (1106) after balloon (1104) is used to dilate the ET (26) and balloon (1104) is deflated. Then, instruments shown in FIGS. 14-19 and FIGS. 22 and 22A may slide toward the clog/debris of the isthmus (29) in order to dislodge it and/or visually confirm the isthmus (29) has been dislodged as described above. It should also be understood that instrument (1100) may be removed from the isthmus (29) and the ET (26) as described above.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An method for cleaning an isthmus of a Eustachian tube (ET) of a patient using an instrument, wherein the instrument comprises a proximal portion, a distal portion, and a shaft extending therebetween, wherein the instrument further comprises a treatment feature disposed at the distal portion, the method comprising: (a) directing the instrument into an oro-nasal cavity of the patient; (b) advancing at least the distal portion of the instrument into an opening of the ET; (c) further advancing the instrument within the ET so that the treatment feature is disposed past, or is coincident with, the isthmus; and (d) moving the treatment feature relative to the isthmus to clean the isthmus.

Example 2

The method of Example 1, wherein the treatment feature comprises an expandable element, and the method further comprises expanding the expandable element once the expandable element is disposed past, or is coincident with, the isthmus.

Example 3

The method of Example 2, wherein the expandable element is configured to not dilate the isthmus or the ET when the expandable element is in the expanded configuration.

Example 4

The method of any one or more of Examples 2 through 3, wherein the expandable element comprises a proximal end and a distal end, wherein expanding the expandable element further comprises moving the distal end of the expandable element proximally relative to the proximal end of the expandable element.

Example 5

The method of any one or more of Examples 2 through 4, wherein the instrument further comprises a handle including an actuator at the proximal portion, wherein expanding the expandable element further comprises actuating the actuator.

Example 6

The method of any one or more of Examples 2 through 5, wherein expanding the expandable element further comprises filling the expandable element with a fluid.

Example 7

The method of any one or more of Examples 1 through 6, wherein moving the treatment feature comprises retracting the treatment feature toward the opening.

Example 8

The method of any one or more of Examples 1 through 6, further comprising: (a) introducing a balloon catheter into the oro-nasal cavity; (b) advancing the balloon catheter including an expandable balloon into the opening of the ET; and (c) dilating the ET with the expandable balloon.

Example 9

The method of Example 8, further comprising: (a) inserting the instrument into a lumen of the balloon catheter; and (b) advancing the balloon catheter and the instrument into the opening of the ET as a unit.

Example 10

The method of any one or more of Examples 8 through 9, wherein inserting the instrument into a lumen of the balloon catheter further comprises advancing the instrument within the lumen of the balloon catheter so that at least the treatment feature protrudes from the distal end of the balloon catheter.

Example 11

The method of Example 10, wherein moving the treatment feature relative to the isthmus to clean the isthmus further comprises moving the treatment feature and the balloon catheter as a unit.

Example 12

The method of any one or more of Examples 8 through 11, wherein the step of dilating the ET is performed prior to the step of moving the treatment feature relative to the isthmus to clean the isthmus.

Example 13

The method of any one or more of Examples 8 through 12, further comprising introducing a guide catheter into the oro-nasal cavity, wherein introducing the balloon catheter into the oro-nasal cavity is performed by introducing the balloon catheter through a lumen of the guide catheter.

Example 14

The method of any one or more of Examples 1 through 13, further comprising (a) illuminating one or both of the ET or the isthmus with a light source; and (b) examining an ear of the patient to determine the presence of light passing through the ET and/or isthmus to assess the extent to which the ET and/or isthmus is obstructed.

Example 15

The method of Example 14, wherein illuminating the ET with a light source further comprises illuminating the ET with a light source disposed on the instrument.

Example 16

A system for cleaning an isthmus of a Eustachian tube (ET) of a patient, the system comprising: (a) a balloon catheter, comprising: (i) a shaft including a proximal portion, a distal portion, and a lumen, and (ii) an expandable balloon disposed at the distal portion of the shaft; and (b) an isthmus cleaning instrument, comprising: (i) a shaft including a proximal portion and a distal portion, (ii) a handle at the proximal portion of the shaft, and (iii) a treatment feature at the distal portion of the shaft, wherein the treatment feature is configured to remove a clog or debris from an isthmus of an ET; wherein the instrument is configured to be received within the lumen of the balloon catheter; wherein the instrument is sized and configured such that at least a portion of the treatment feature is extendable distally out of the distal end of the balloon catheter.

Example 17

The system of Example 16, further comprising a proximal connector at the proximal portion of the balloon catheter, wherein the isthmus cleaning instrument is configured to be received within the lumen of the balloon catheter until a transition portion of the isthmus cleaning instrument abuts the proximal connector.

Example 18

The system of Example 17, wherein the instrument is sized and configured such that when the transition portion abuts the proximal connector, at least a portion of the treatment feature extends distally out of the distal end of the balloon catheter.

Example 19

The system of any one or more of Examples 17 through 18, wherein the expandable element comprises an expandable balloon, wherein the expandable balloon of the isthmus cleaning instrument has an expanded outer diameter that is smaller than an expanded outer diameter of the balloon of the balloon catheter.

Example 20

A system for cleaning an isthmus of a Eustachian tube (ET) of a patient, the system comprising: (a) a guide catheter comprising a shaft including a proximal portion, a distal portion, and a first lumen extending therebetween, wherein the guide catheter further comprises a bend at the distal portion, wherein the bend is configured to provide access to an opening in the ET when the guide catheter is inserted into a nostril of the patient; (b) a balloon catheter comprising a shaft including a proximal portion, a distal portion, and a second lumen therebetween, wherein the balloon catheter comprises an expandable balloon disposed at the distal portion of the balloon catheter and a proximal connector at the proximal portion of the balloon catheter, wherein the shaft of the balloon catheter is sized and configured to be received in the first lumen of the guide catheter and is configured to bend according to the bend in the guide catheter; and (c) an instrument comprising: (i) a shaft including a proximal portion and a distal portion and being configured to bend according to the bend in the guide catheter, and (ii) a treatment feature at the distal portion of the shaft, wherein the treatment feature is sized and configured to traverse the isthmus in order to clean the isthmus

VI. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, examples, examples, etc. described herein may be combined with any one or more of the other teachings, expressions, examples, examples, etc. that are described herein. The above-described teachings, expressions, examples, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various examples of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, examples, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method for cleaning an isthmus of a Eustachian tube (ET) of a patient using an instrument, wherein the instrument comprises a proximal portion, a distal portion, and a shaft extending therebetween, wherein the instrument further comprises a treatment feature disposed at the distal portion, the method comprising:
   (a) directing the instrument into an oro-nasal cavity of the patient;
   (b) advancing at least the distal portion of the instrument into an opening of the ET;
   (c) further advancing the instrument within the ET so that the treatment feature is disposed past, or is coincident with, the isthmus; and
   (d) moving the treatment feature relative to the isthmus while atraumatically frictionally engaging the isthmus to thereby clean the isthmus by removing debris without damaging the isthmus.

2. The method of claim 1, wherein the treatment feature comprises an expandable element, and the method further comprises expanding the expandable element once the expandable element is disposed past, or is coincident with, the isthmus.

3. The method of claim 2, wherein the expandable element is configured to not dilate the isthmus or the ET when the expandable element is in the expanded configuration.

4. The method of claim 2, wherein the expandable element comprises a proximal end and a distal end, wherein expanding the expandable element further comprises moving the distal end of the expandable element proximally relative to the proximal end of the expandable element.

5. The method of claim 2, wherein the instrument further comprises a handle including an actuator at the proximal portion, wherein expanding the expandable element further comprises actuating the actuator.

6. The method of claim 1, further comprising verifying that a marker disposed at a distal end of the treatment feature is disposed past, or is coincident with, the isthmus.

7. The method of claim 2, wherein moving the expandable element relative to the isthmus causes no permanent dilation of the isthmus.

8. The method of claim 1, further comprising
   (a) illuminating one or both of the ET or the isthmus with a light source; and
   (b) examining an ear of the patient to determine the presence of light passing through the ET and/or isthmus to assess the extent to which the ET and/or isthmus is obstructed.

9. The method of claim 8, wherein illuminating the ET with a light source further comprises illuminating the ET with a light source disposed on the instrument.

10. The method of claim 1, further comprising:
    (a) introducing a balloon catheter into the oro-nasal cavity;
    (b) advancing the balloon catheter including an expandable balloon into the opening of the ET; and
    (c) dilating the ET with the expandable balloon.

11. The method of claim 10, further comprising:
    (a) inserting the instrument into a lumen of the balloon catheter; and
    (b) advancing the balloon catheter and the instrument into the opening of the ET as a unit.

12. The method of claim 11, wherein inserting the instrument into the lumen of the balloon catheter further comprises advancing the instrument within the lumen of the balloon catheter so that at least the treatment feature protrudes from the distal end of the balloon catheter.

13. The method of claim 12, wherein moving the treatment feature relative to the isthmus to clean the isthmus further comprises moving the treatment feature and the balloon catheter as a unit.

14. The method of claim 10, wherein the step of dilating the ET is performed prior to the step of moving the treatment feature relative to the isthmus to clean the isthmus.

15. The method of claim 10, further comprising introducing a guide catheter into the oro-nasal cavity, wherein introducing the balloon catheter into the oro-nasal cavity is performed by introducing the balloon catheter through a lumen of the guide catheter.

16. A system for cleaning an isthmus of a Eustachian tube (ET) of a patient, the system comprising:
 (a) a balloon catheter, comprising:
  (i) a shaft including a proximal portion, a distal portion, and a lumen, and
  (ii) an expandable balloon disposed at the distal portion of the shaft; and
 (b) an isthmus cleaning instrument, comprising:
  (i) a shaft including a proximal portion and a distal portion,
  (ii) a handle at the proximal portion of the shaft, and
  (iii) a treatment feature at the distal portion of the shaft, wherein the treatment feature includes proximal and distal ends, wherein the treatment feature is configured to expand uniformly in a radially outward direction from the shaft from a non-expanded configuration to an expanded configuration, wherein the distal end of the treatment feature is configured to move proximally along the shaft while the proximal end of treatment feature remains stationary relative to the shaft, wherein the treatment feature is sized and configured to enter an isthmus of an ET when in the non-expanded configuration, wherein the treatment feature is sized and configured to atraumatically sweep or atraumatically scrape against a wall of the isthmus of the ET when in the expanded configuration without damaging the isthmus;
 wherein the instrument is configured to be received within the lumen of the balloon catheter;
 wherein the instrument is sized and configured such that at least a portion of the treatment feature is extendable distally out of the distal end of the balloon catheter.

17. The system of claim 16, further comprising a proximal connector at the proximal portion of the balloon catheter, wherein the isthmus cleaning instrument is configured to be received within the lumen of the balloon catheter until a transition portion of the isthmus cleaning instrument abuts the proximal connector.

18. The system of claim 17, wherein the instrument is sized and configured such that when the transition portion abuts the proximal connector, at least a portion of the treatment feature extends distally out of the distal end of the balloon catheter.

19. A method for cleaning an isthmus of a Eustachian tube (ET) of a patient using an instrument, wherein the instrument comprises a proximal portion, a distal portion, and a shaft extending therebetween, wherein the instrument further comprises a treatment feature disposed at the distal portion, the method comprising:
 (a) introducing a balloon catheter into the oro-nasal cavity of the patient;
 (b) inserting the instrument into a lumen of the balloon catheter;
 (c) advancing the balloon catheter and the instrument into the opening of the ET as a unit;
 (d) dilating the ET with an expandable balloon;
 (e) further advancing the instrument within the ET so that the treatment feature is disposed past, or is coincident with, the isthmus; and
 (f) moving the treatment feature relative to the isthmus while frictionally engaging the isthmus to thereby clean the isthmus.

20. The method of claim 19, wherein inserting the instrument into the lumen of the balloon catheter occurs before introducing the balloon catheter into the oro-nasal cavity of the patient.

* * * * *